United States Patent [19]
Kadkade

[11] Patent Number: 6,127,181
[45] Date of Patent: *Oct. 3, 2000

[54] CRYOPRESERVATION OF PLANT CELLS

[75] Inventor: Prakash G. Kadkade, Marlboro, Mass.

[73] Assignee: Phyton, Inc., Ithaca, N.Y.

[*] Notice: This patent is subject to a terminal disclaimer.

[21] Appl. No.: 08/659,997

[22] Filed: Jun. 7, 1996

Related U.S. Application Data

[63] Continuation-in-part of application No. 08/486,204, Jun. 7, 1995.

[51] Int. Cl.$^7$ .......................... A01N 63/00; A01N 65/00; C12N 5/04
[52] U.S. Cl. ................. 435/420; 435/1.3; 435/430.1; 424/93.7
[58] Field of Search .................. 435/1.3, 420–430.1; 424/93.7

[56] References Cited

U.S. PATENT DOCUMENTS 5,071,741 12/1991 Brockbank .................................. 435/1

FOREIGN PATENT DOCUMENTS 0147236 12/1984 European Pat. Off. .

OTHER PUBLICATIONS

Fretz, et al, "Cryopreservation of Embryogenic Suspension Cultures of Barley", *Bot. Acta*, vol. 105, (1992) pp. 140–145.
Lu, et al, "Cryopreservation of Millet", *J. Plant Physiol.*, vol. 139 (1992), pp. 295–298.
Uragami, et al, "Cryopreservation of Asparagus", *JARQ*, vol. 27 (1993), pp. 112–115.
Reuff, et al, "Cryopreservation of *Coleus blumei* Suspension and Callus Cultures", *J. Plant Physiol.*, vol. 133 (1988), pp. 414–418.
Dussert, et al, "Cryopreservation of Grape Embryogenic Cell Suspensions 2: Influence of Post–Thaw Culture Conditions and Application to Different Strains", *Cryo–Letters*, vol. 13 (1992), pp. 15–22.
Wang, et al, "Cryopreservation of Embryogenic Cell Suspensions in Festuca and Lolium Species", *Plant Science*, vol. 103 (1994), pp. 93–106.
McClellan et al, "The Response of four Cultured Plant Cell Lines to Freezing and Thawing in the Presence or Absence of Cryoprotectant Mixtures", *Cryo–Letters*, vol. 11 (1990), pp. 189–197.
Nishizawa, et al, "Cryopreservation of asparagus (*Asparagus officinalis* L.) Cryogenic Suspension Cells and subsequent Plant Regeneration by Vitrification", *Plant Science*, vol. 91 (1993) pp. 67–73.
Panis, et al, "Cryopreservation of Musa Suspension Cultures and Subsequent Regeneration of Plants", *Cryo–Letters*, vol. 11 (1990), pp. 337–350.
Dussert, et al, "Cryopreservation of Grape Embryogenic Cell Suspensions: 1–Influence of Pretreatment, Freezing and Thawing Conditions", *Cryo–Letters*, vol. 12 (1991), pp. 287–298.
Fretz, et al, "Cryopreservation of In vitro Cultures of Barley (*Hordeum vulgare* L. and *H. murinum* L.) and Transgenic Cells of Wheat (*Triticum asestivum* L.)" *J Plant Physiol.*, vol. 146 (1995), pp. 489–496.
Seitz, et al, Growth and Ginenoside Patterns of Cryopreserved *Panax ginseng* Cell Cultures, *J. Plant Physiol.*, vol. 131 (1987), pp. 215–223.
XP002029641—*Advances in Low–Temperature Biology*, vol. 1, 1992, Peter L. Steponkus, Cornell University, Ithaca, NY.
XP000646623—*Vitrification of Plant Cell Suspensions*, Chapter 12, pp. 113–119, 1995, P.J. Reinhoud, A. Uragami, A. Sakai, F. Van Iren.
XP000646465—Cryopreservation, [7], 1994, pp. 147–167, Erica E. Benson.

*Primary Examiner*—David M. Naff
*Assistant Examiner*—Deborah K. Ware
*Attorney, Agent, or Firm*—Baker & Botts, LLP

[57] ABSTRACT

The present invention relates to methods for cryopreserving plant cells and to methods for recovering viable plant cells from long or short term cryopreservation. Plant cells to be cryopreserved can be grown in culture and pretreated with a solution containing an cryoprotective agent and, optionally, a stabilizer. Stabilizers are preferably membrane stabilizers such as ethylene inhibitors, oxygen radical scavengers and divalent cations. Cells can also be stabilized by subjecting the culture to a heat shock. Pretreated cells are acclimated to a reduced temperature and loaded with a cryoprotective agent such as DMSO, propylene glycol or polyethylene glycol. Loaded cells are incubated with a vitrification solution which, for example, comprises a solution with a high concentration of the cryoprotective agent. Vitrified cells retain less than about 20% water content and can be frozen at cryopreservation temperatures for long periods of time without significantly altering the genotypic or phenotypic character of the cells. Plant cells may also be cryopreserved by lyophilizing cells prior to exposure to a vitrification solution. The combination of lyophilization and vitrification removes about 80% to about 95% of the plant cell's water. Cells can be successfully cryopreserved for long periods of time and viably recovered. The invention also relates to methods for the recovery of viable plant cells from cryopreservation. Cells are thawed to about room temperature and incubated in medium containing a cryoprotective agent and a stabilizer. The cryoprotective agent is removed and the cells successfully incubated and recovered in liquid or semi-solid growth medium.

28 Claims, 9 Drawing Sheets

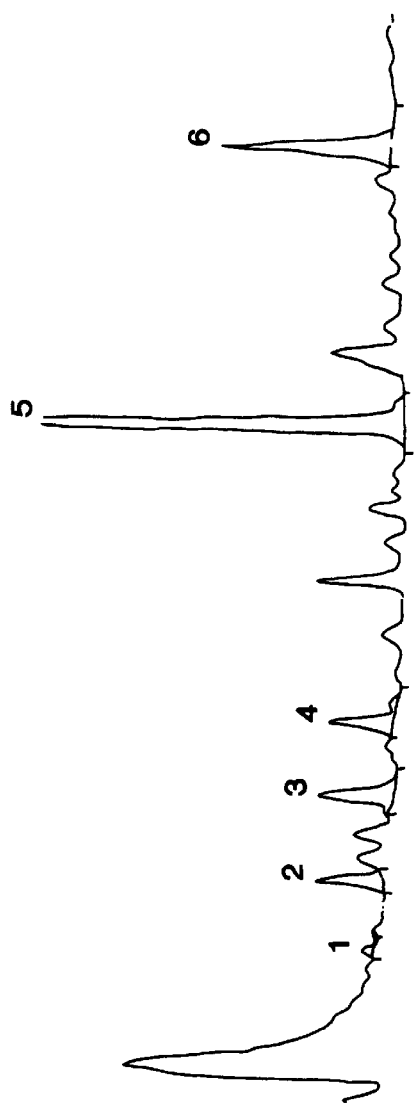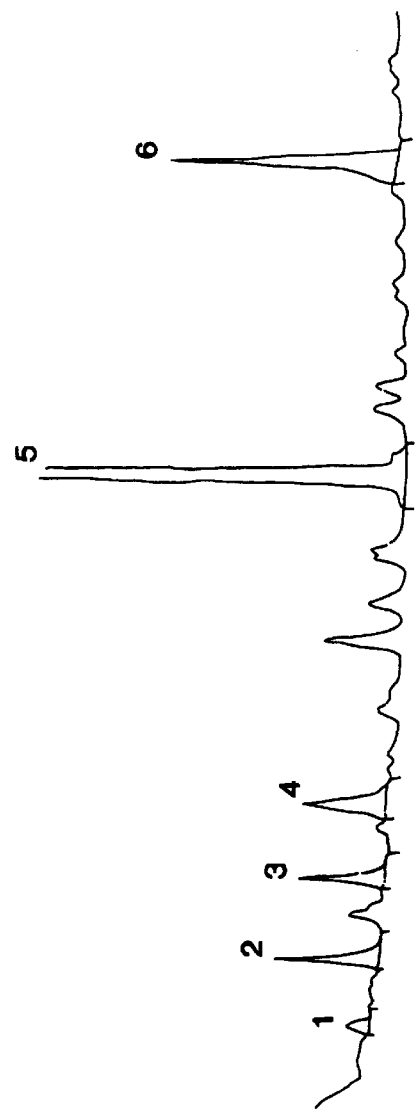

CRYOPRESERVATION OF PLANT CELLS

REFERENCE TO RELATED APPLICATIONS

This application is a continuation-in-part of U.S. patent application Ser. No. 08/486,204, filed Jun. 7, 1995.

BACKGROUND OF THE INVENTION

1. Field of the Invention

The present invention relates to methods for the cryopreservation of plant cells and to methods for the recovery of plants cells which have been cryopreserved. The invention also relates to plants, viable plant cells and plant cells cultures which have been successfully recovered from cryopreservation.

2. Description of the Background

Cryopreservation is based on the reduction and subsequent arrest of metabolic functions of biological material stored at ultra-low temperatures. Cryogenic preservation of plants and plant cells for extended periods without genetic change and the subsequent recovery of normal plant cells with unaltered characteristics and biosynthetic ability has important implications in plant breeding, biomedical research and genetic engineering. At the temperature of liquid nitrogen (−196° C.) almost all metabolic activities the cell ceases and cells can be maintained in this suspended, but viable state for extended periods.

Plant cells are cryopreserved to avoid loss by contamination, to minimize genetic change in continuous cell lines, and to avoid aging and transformation in finite cell lines. Traditional methods for preservation of a desirable plant characteristic involve establishment of colonies of plants in the field because many plants do not breed true from seeds. These field plant depositories demand large inputs of labor and land and incur high risks of loss due to weather, disease or other hazards. An alternative to a field colony is the establishment of an in vitro collection of plant tissue under normal or limited growth conditions. For long-term storage, elimination of routine subculturing is desirable because of concerns with mutation, contamination, labor cost and risk of human error associated with tissue culture.

Most biological materials, including plants, cannot survive freezing and thawing from cryogenic temperatures without cryoprotective agents and procedures. A number of cryopreservatives possess properties which can protect a cell from the damaging effects of cryogenic freezing. The essence of cryopreservation is to effect cell dehydration and concentration of the cytosol in a controlled and minimally injurious manner so that ice crystallization in the cytosol is precluded or minimized during, for example, quenching in liquid nitrogen.

In conventional cryopreservation procedures, cell dehydration is effected by freeze-induced concentration of the suspending medium. Deleterious effects of dehydration are mitigated by the presence of cryoprotective agents. Specimens such as cells and organs are equilibrated in a solution containing a cryopreservation agent such as dimethylsulfoxide (DMSO) or ethylene glycol. The suspension is cooled and seeded with an ice crystal at a temperature slightly below its freezing point. The suspension is cooled again at an optimum rate to an intermediate sub-zero temperature such as between about −30° C. and about −40° C. and finally quenched in liquid nitrogen.

While routine cryogenic preservation of microorganisms, zygotes and animals derived from zygotes is possible, the cryopreservation of plant cells is far from routine and often, different protocols for individual species of plants are necessary.

Taxus trees produces taxol, a diterpenoid alkaloid originally isolated from the bark of the Pacific yew, *Taxus brevifolia* (M. C. Wani et al., J. Am. Chem. Soc. 93:2325–27, 1971). Experiments have demonstrated that this compound effectively inhibits the polymerization of microtubules of mammalian cells without undue toxicity and, as such, is an effective anti-tumorigenic agent. Clinical trails identified taxol as extremely effective against refractory ovarian, breast and other cancers. As such, taxol is a breakthrough in chemotherapy because of its rather unique, but basic mechanism of action which is fundamentally distinct from that of conventional chemotherapeutic agents (L. A. Rowinsky et al., J. Natl. Cancer Instit. 82:1247–59, 1990).

The most daunting variable in the taxol equation so far is supply. It takes three to six, 100 year old Pacific yews to treat one patient because average yields of taxol are low (Witherup et al., 1990). The production of an amount of taxol needed for treatment and testing will require the destruction of tens of thousands of yews. The yew population has been rendered nearly extinct by logging and as the number of Pacific yews dwindles, medical research must look for other forms of supply for taxol. The usefulness of taxol, as well as many other compounds which may be propagated or harvested in plant cells, has fueled an interest in culturing taxus and other plant cells.

The culturing of plant cells for their biosynthetic ability poses special problems for current technology. Prolonged culturing of plant cells often results in a loss of biosynthetic ability which had been present in the original isolates (Dhoot et al., Ann. Bot. 41:943–49, 1977; Barz et al., Ber. Dtsch. Bot. Ges. 94:1–26, 1981). Phenotypic alterations also arise which further complicate cell culturing. A protocol for freezing plant cells, especially taxus cells, is an important step in the development of biosynthetic methods for production of useful plant alkaloids such as taxol.

SUMMARY OF THE INVENTION

The present invention overcomes the problems and disadvantages associated with current strategies and designs and provides novel methods for cryopreservation and for the recovery of viable cryopreserved plant cells.

One embodiment of the invention is directed to methods for the cryopreservation of plant cells. Plant cells, which may be gymnosperms or angiosperms, are pretreated with a cryoprotective agent and a stabilizer, and acclimated to a reduced temperature. Stabilizers such as, for example, divalent cations, in part, protect cellular membranes from rupture. Pretreatment may also include an ethylene inhibitor, such as an ethylene action inhibitor or an ethylene biosynthesis inhibitor. Pretreated plant cells are vitrified and frozen at a cryopreservation temperature. Divalent cations may also be included in the vitrification step or a loading step. Acclimated cells are loaded with a loading agent which may be the same as the vitrifying agent and the loaded cells vitrified with a vitrification solution. Vitrified plant cells are frozen at cryopreservation temperatures, such as, between about −70° C. to about −200° C. or less.

Another embodiment of the invention is directed to methods for cryopreserving plant cells. Plant cells to be cryopreserved are pretreated with a cryoprotective agent, an ethylene inhibitor, divalent cations or heat-shock protein, and acclimated to a reduced temperature. The ethylene inhibitor may be an ethylene action inhibitor or an ethylene biosynthesis inhibitor. Acclimated plant cells are vitrified and frozen at a cryopreservation temperature.

Another embodiment of the invention is directed to methods for cryopreserving plant cells. Plant cells to be cryopreserved are cultured in media comprising a vitrifying agent and a stabilizer at a reduced temperature for a first period of time. The cultured plant cells are further cultured in media containing an increased concentration of the vitrifying agent for a second period of time. Plant cells vitrified in the higher concentration of vitrifying agent are frozen at a cryopreservation temperature.

Another embodiment of the invention is directed to methods for cryopreserving plant cells. Plant cells to be cryopreserved are lyophilized by vacuum evaporation and vitrified in a vitrifying solution. Lyophilization removes about 60% of the water from the cells and in combination with vitrification can remove up to about 95%. The vitrified and lyophilized plant cells are frozen and stored at a cryopreservation temperature by, for example, quenching the cells into liquid nitrogen.

Another embodiment of the invention is directed to methods for cryopreserving plant cells. Plant cells to be cryopreserved are pretreated with a heat shock. Heat shock induces the expression of proteins that, in part, stabilize cellular membranes from rupture. Pretreatment may also include an ethylene inhibitor, such as an ethylene action inhibitor or an ethylene biosynthesis inhibitor. Pretreated plant cells are vitrified and frozen at a cryopreservation temperature. Divalent cations may also be included in the pretreatment or vitrification steps, or in a loading step.

Another embodiment of the invention is directed to methods for recovering plant cells from cryopreservation. Plant cells are cryopreserved according to the methods of the invention. Thawed plant cells are warmed to a temperature above freezing and incubated in a media comprising a cryoprotective agent and a stabilizer. The osmotic agent is removed and viable plant cells recovered.

Another embodiment of the invention is directed to methods for recovering plant cells from cryopreservation. Plant cells are cryopreserved according to the methods of the invention. Thawed plant cells are warmed to a temperature above freezing and incubated in a media comprising ethylene inhibitors, oxygen radical scavengers, divalent cations, cryoprotective agents or combinations of these substances. Viable plant cells are recovered that show vigorous recovery regrowth and can be quickly established into cell suspensions.

Another embodiment of the invention is directed to methods for recovering cryopreserved plant cells from cryopreservation. Cryopreserved plant cells are thawed to a temperature above freezing and incubated in media comprising a cryoprotective agent and a stabilizer. The cryoprotective agent is removed such as by dilution of the mixture or pelleting of the cells and viable plant cells recovered.

Another embodiment of the invention is directed to viable plant cells which have been cryopreserved by the method of the invention. Cryopreserved plant cells are not significantly genetically or phenotypically altered by cryopreservation.

Another embodiment of the invention is directed to methods for recovering cryopreserved plant cells in suspension. Cryopreserved plant cells are thawed to a temperature above freezing. Thawed plant cells are incubated in liquid suspension and viable cells recovered in liquid media without a need for solid or semi-solid culture.

Another embodiment of the invention is directed to viable plants and plant cells cryopreserved and to viable plants and plant cells recovered by the methods of the invention. Cells are not significantly genotypically or phenotypically altered by the cryopreservation process and have a high proportion of survival.

Other embodiments and advantages of the invention are set forth, in part, in the description which follows and, also in part, will be obvious from this description or may be learned from the practice of the invention.

DESCRIPTION OF THE FIGURES

FIG. 6 Chromatograms of (A) cells cryopreserved for 6 months in comparison with (B) non-cryopreserved cells.

DESCRIPTION OF THE INVENTION

Figure 1A:
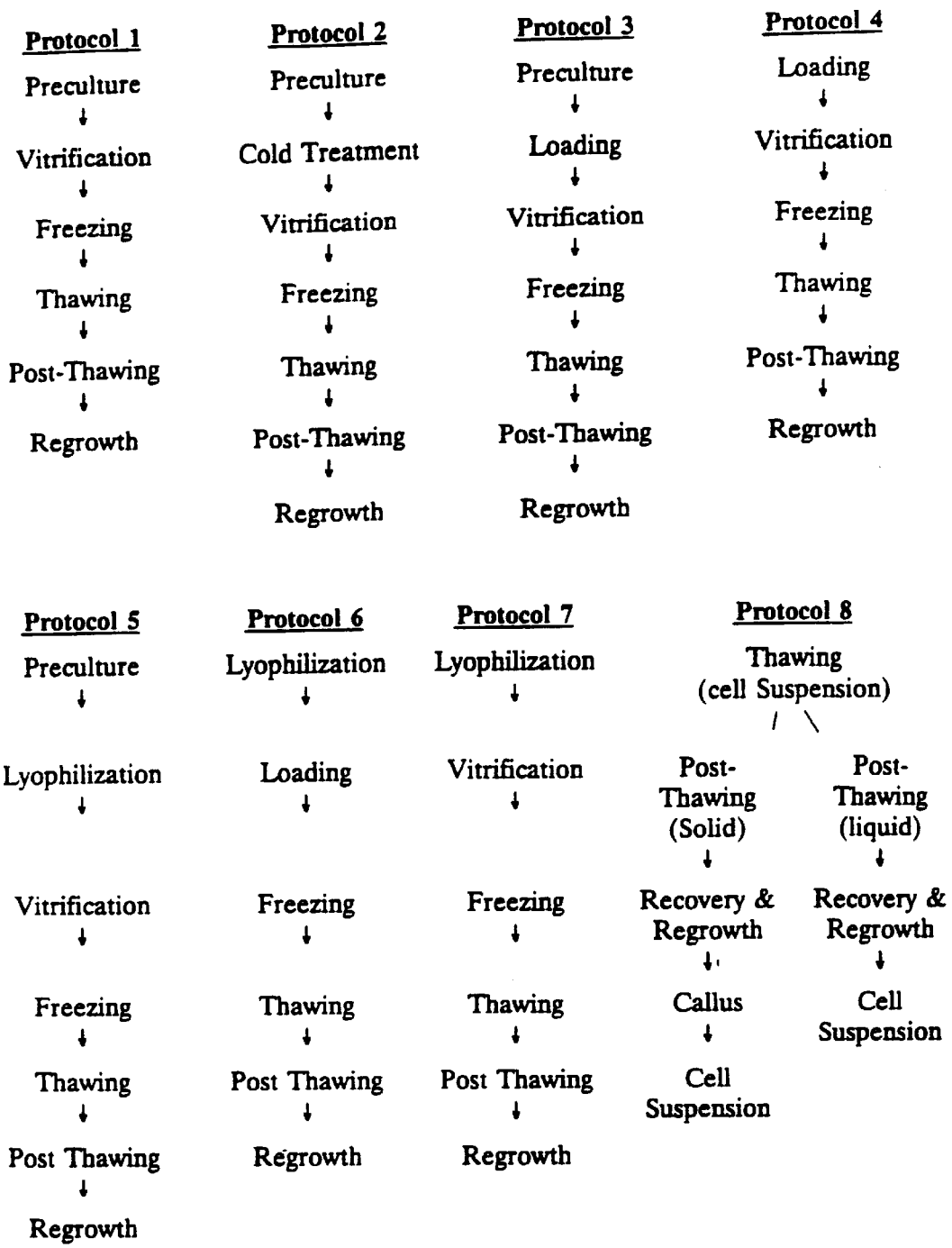
FIGS. 1 (A, B and C) Schematics of various cryopreservation and recovery protocols.

As embodied and broadly described herein, the present invention is directed to methods for the cryopreservation of plant cells, methods for the recovery of cryopreserved plant cells and viable plant cells which have been successfully recovered from cryopreservation.

Plant cells are increasing useful for the production of recombinant protein or unique products and chemical agents which are specific to plants or to the enzymatic pathways of plant cells. Plant cells such as callus cultures can be maintained in a continuous state through repeated sub-culturing. However, sub-culturing frequently results in increased ploidy, an increased risk of contamination, an accumulation of spontaneous mutations, a decline and loss of morphogenetic potential, a reduction of biosynthetic capacity for product formation, a reversion of selected lines to wild-types, aging and transformation infinite cell lines and unintentional selection of undesirable phenotypes. Each of these factors can severely impede the exploitation of cell culture systems for commercial production of valuable compounds.

While animal tissue cultures cells have been routinely cryopreserved for many years, similar cryopreservation techniques for plant cells has proven to be far more difficult. Plant cells and, in particular, plant cells in culture, exhibit an array of heterogeneity with respect to growth rate, doubling time, mitotic index, cell synchrony, nuclear to cytoplasmic ratio and extent of vacuolation. Cells present in any give culture also exhibit a variety of physiological and morphological variations. Further, plant cell suspensions and adherent cell cultures require different protocols for cryopreservation. In addition, if performed improperly, cryopreservation can induce the very mutations which the process is attempting to prevent.

Surprisingly, it has been discovered that by using a series of steps and specific agents, plant cells of most any genus and species can be cryopreserved and successfully recovered. These methods are based on the observations that successful plant cell cryopreservation involves the removal of substantial amounts of water from the cells and that under appropriate conditions, significant amounts of water can be removed without seriously effecting cell viability. Cryopreservation protocols developed are highly successful at storing, maintaining and retrieving viable cells in a routine and reproducible manner. These protocols can be established in routine unit operations to create germplasm storage and cell bank management systems. In addition, cells can be recovered entirely in liquid suspension, a process previously thought not to be possible with plant cultures. Products harvested from cryopreserved cells do not significantly vary from the original or parent cell as there has been little if any phenotypic or genotypic drift, particularly with respect to respect to growth and viability, product formation and cell biomass proliferation. Variances are determined from observable or quantifiable phenotypic or morphological alterations. Those alterations become significant when they decrease the phenotypic parameter by more than a small degree.

One embodiment of the invention is directed to methods for the cryopreservation of plant cells. These methods are surprisingly reproducible and applicable to many types of plant cells. As such, they will be markedly useful for the production of materials which require government or agency standards of reproducibility.

Figure 1B:
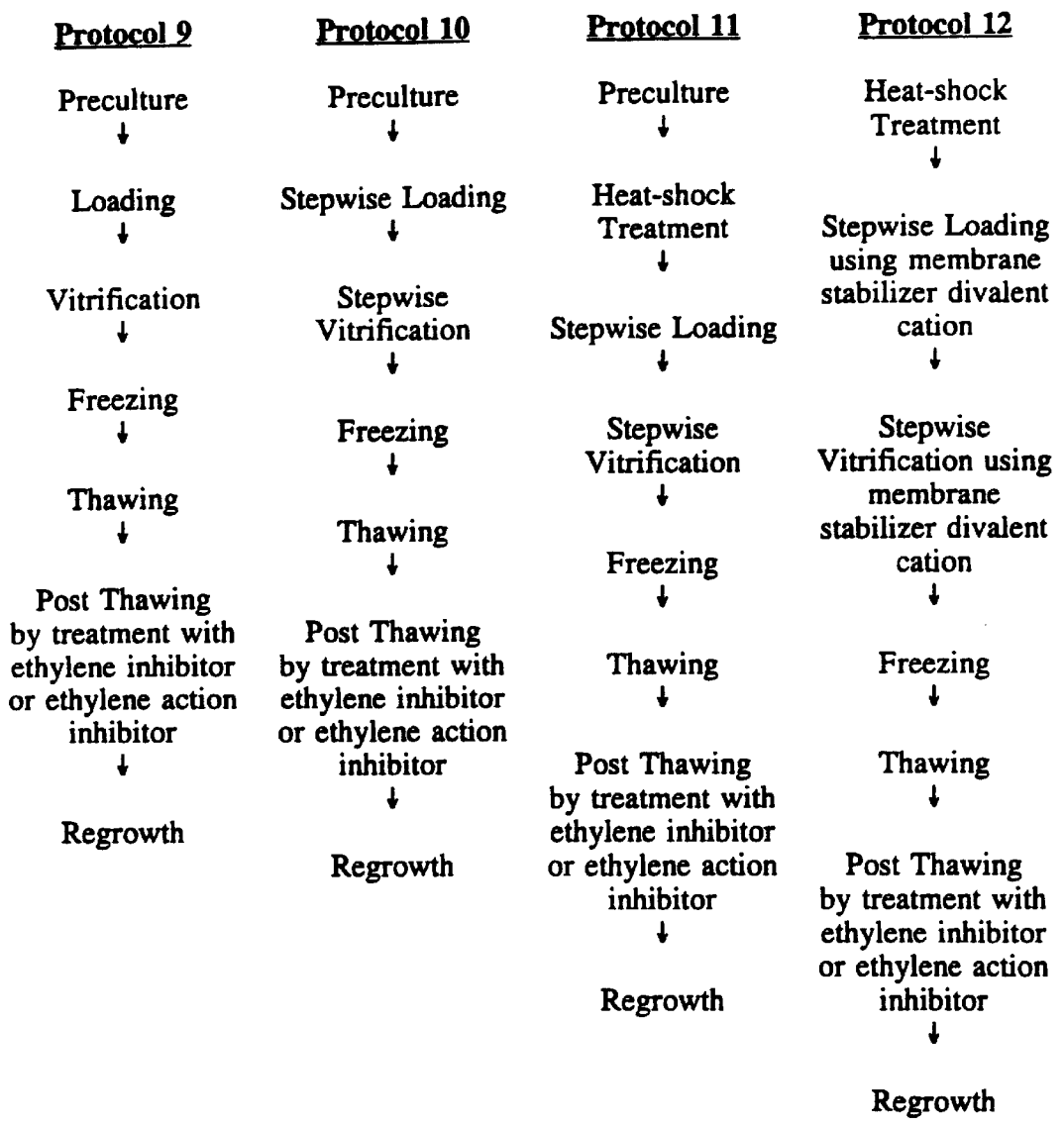
Figure 1C:
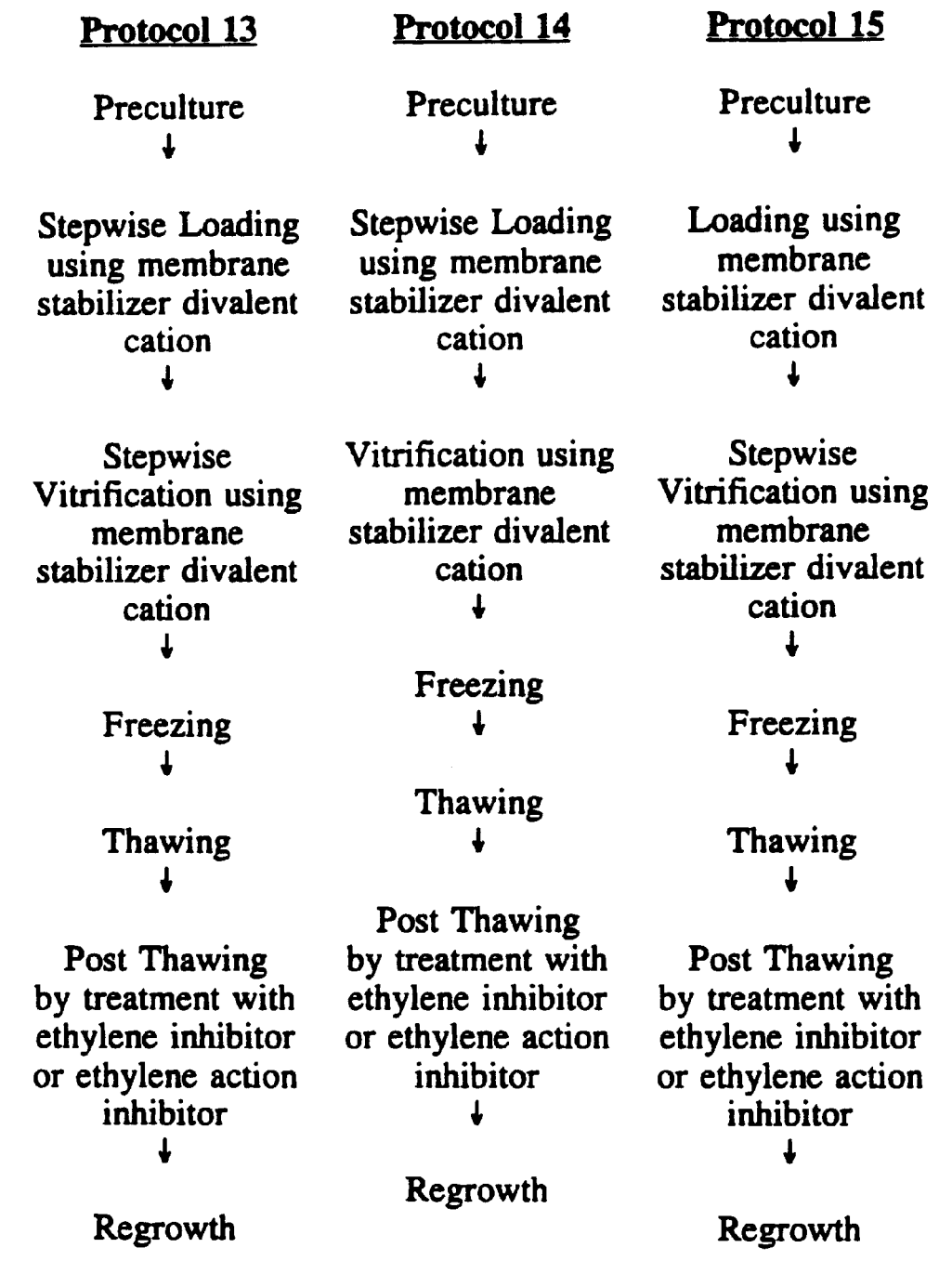

The basic process involves the removal of substantial amounts of water from the cell by a combination of pre-treatment (e.g. preculture with cryopreservant or stabilizers such as divalent cations, radical scavengers or heat shock), cold acclimating, stepwise or single dose loading or vitrifying, lyophilizing, freezing and thawing steps. A wide variety of combinations of these steps is possible and every step is not necessarily required for the successful cryopreservation and recovery of viable plant cells that retain the characteristics and growth properties that made them desirable. Some of the possible combinations of the various embodiments of the steps are schematically depicted in FIGS. 1A, 1B and 1C, although it is understood that these variations are only exemplary. Each type of plant (e.g. class, order, family, genus, species, subspecies or variety) will more than likely have its own set of preferred conditions that will maximize recovery from cryopreservation. From the selected variations disclosed herein, optimal parameters for cryopreservation can be easily determined.

Most any plant cell can be successfully cryopreserved and recovered using these processes including the gymnosperms and the angiosperms. Specific types of gymnosperms which can be cryopreserved include species of the genera Abies (firs), Cypressus (cypresses), Ginkgo (maidenhair tree), Juniperus (juniper), Picea (spruce), Pinus (pine), Pseudotsuga (Douglas fir), Sequoia, Taxus (yew), Tsuga (hemlock) or Zamia (cycad). Some of the more useful species of Taxus include *T. baccata, T. brevifolia, T. canadensis, T. chinensis, T. cuspidata, T. floridana, T. globosa, T. media, T. nucifera* and *T. wallichiana*. Angiosperms which can be preserved include monocotyledon plant cells and dicotyledon plant cells. Monocotyledon plant cells include a variety of species of the genus Avena (oat), Cocos (coconut), Dioscorea (yam), Hordeum (bareley), Musa (banana), Oryza (rice), Saccharum (sugar cane), Sorghum (sorghum), Triticum (wheat) and Zea (corn). Dicotyledon plants include species of the genus Achyrocline, Atropa, Brassica (mustard), Berberis, Sophora, Legume, Lupinus, Capsicum, Catharanthus, Conospermum, Datura, Daucus (carrot), Digitalis, Echinacea, Eschscholtzia, Glycine (soybean), Gossypium (cotton), Hyoscyamus, Lycopersicum (tomato), Malus (apple), Medicago (alfalfa), Nicotiana, Panax, Pisum (pea), Rauvolfia, Ruta, Solanum (potato) and Trichosanthes.

Plant cells may be freshly harvested specimens from the field as new growth needles, leaves, roots, bark, stems, rhizomes, callus cells, protoplasts, cell suspensions, organs or organ systems, meristems such as apical meristems, seeds or embryos. Generally, low passage cells and primary cultures show greater ultimate viability in culture or upon recovery from cryopreservation. Alternatively, sample cells may be obtained from established in vitro cultures. Cultures may have been long established or only recently adapted to in vitro conditions of, for example, specific temperatures, particular light intensities or special growth or maintenance mediums. Such cells may be maintained as suspension cells or by growth on semi-solid nutrient medium.

Suspension cultures can be derived from callus cultures of a Taxus species or from thawed cryopreserved cells of a Taxus species. Low passage primary cell lines are very valuable to preserve as these cultures may exhibit unique characteristics which are lost with extended time in culture. Many of these cell lines express diterpenoids such as the diterpenoid alkaloid taxane, the ester side chain modified taxane, taxol (molecular weight 853), and a variety of other modifications of taxane (baccatin or 10-deactylbaccatin).

Taxus cells for culture can be obtained from any plant material. Collections can be made from over North America as well as other continents. Tissue from any part of the plant including bark, cambium, needles, stems, seeds, cones and roots, can be selected and adapted for cell culture. Needles and meristematic regions of plants, especially one to three month old new growth needles are preferred for initiating cell cultures. For example, selected plant tissue is surface-sterilized by immersion in a four liter 10% solution of bleach with 10 drops of Tween 20 added for 20 minutes. Cut tissues explants to very small sizes and cultured.

Taxus cultures typically exhibit variability in growth morphology, productivity, product profiles and other characteristics. As individual cell lines vary in their preferences for growth medium constituents, many different growth media may be used for induction and proliferation of the cell culture. Methods of sterilization, initiation of callus growth, and suspension growth, as well as suitable nutrient media, are well-known to those of ordinary skill in the art.

Taxus suspension cultures are capable of rapid growth rates and high cell densities. Initial cultures of various Taxus species are sub-cultured by transfer into suitable media containing, for example, macro and micro nutrients, organic salts and growth hormones. Liquid cultures are exposed to air and preferably agitated to aerate the medium or air may be bubbled in the medium. Cultures are maintained at a temperature of about 20° C. and at a pH of between about 3 to about 7, and preferably of between about 4 to about 6. Such cultures can be harvested by removal of the growth medium, for example, by filtration or centrifugation. Cells with the highest viability are those at the early lag or early cell division growth phases or recently passed through cell division or mitosis. Generally, 4–10 day old cell suspension of a Taxus species in growth medium, preferably 5–8 day old cell suspensions in growth medium, and more preferably 6–7 day old cell suspensions of a Taxus species in growth medium, are suitable for use.

Each of the basic steps of cryopreservation are presented below:

Pretreatment

Plant cells to be cryopreserved can be pretreated with agents that increase cellular viability by removing harmful substances secreted by the cells during growth or cell death from the culture medium. These agents, referred to as stabilizers herein, include substances that may be naturally occurring or artificially produced and can be introduced directly into the culture medium. Stabilizers include anti-oxidants or radical scavenger chemicals that neutralize the very deleterious effects attributable to the presence of active oxygen species and other free radicals. Such substances are capable of damaging cellular membranes, both internal and external membranes, such that cryopreservation and recovery are seriously compromised. If these substances are not removed or rendered otherwise ineffective, their effects on viability are cumulative over time severely limiting practical storage life. Furthermore, as cells die or become distressed, additional harmful substances are released increasing the damage and death of neighboring cells.

Useful stabilizers include those chemicals and chemical compounds which sequester highly reactive and damaging molecules such as oxygen radicals. Specific examples of these radical scavengers and anti-oxidants include reduced glutathione, 1,1,3,3-tetramethylurea, 1,1,3,3-tetramethyl-2-thiourea, sodium thiosulfate, silver thiosulfate, betaine, N,N-dimethylformamide, N-(2-mercaptopropionyl) glycine, β-mercaptoethylamine, selenomethionine, thiourea, propylgallate, dimercaptopropanol, ascorbic acid, cysteine, sodium diethyl dithiocarbomate, spermine, spermidine, ferulic acid, sesamol, resorcinol, propylgallate, MDL-71, 897, cadaverine, putrescine, 1,3- and 1,2-diaminopropane, deoxyglucose, uric acid, salicylic acid, 3- and 4-amino-1,2, 4-triazol, benzoic acid, hydroxylamine and combinations and derivatives of such agents.

Another group of stabilizers include agents that hinder or substantially prevent ethylene biosynthesis and/or ethylene action. Certain of these compounds also have scavenger properties as well. Effects of ethylene inhibitors are substantial when the expression or action of ethylene is sufficiently affected so as to increase cell recovery in the cryopreservation process. It is well known that many plant cells emit ethylene when stressed. Ethylene damages cells and leads to cell death. Prevention of either the generation of ethylene or the action of ethylene will further enhance cell viability and cell recovery from the cryopreservation process.

Figure 2:
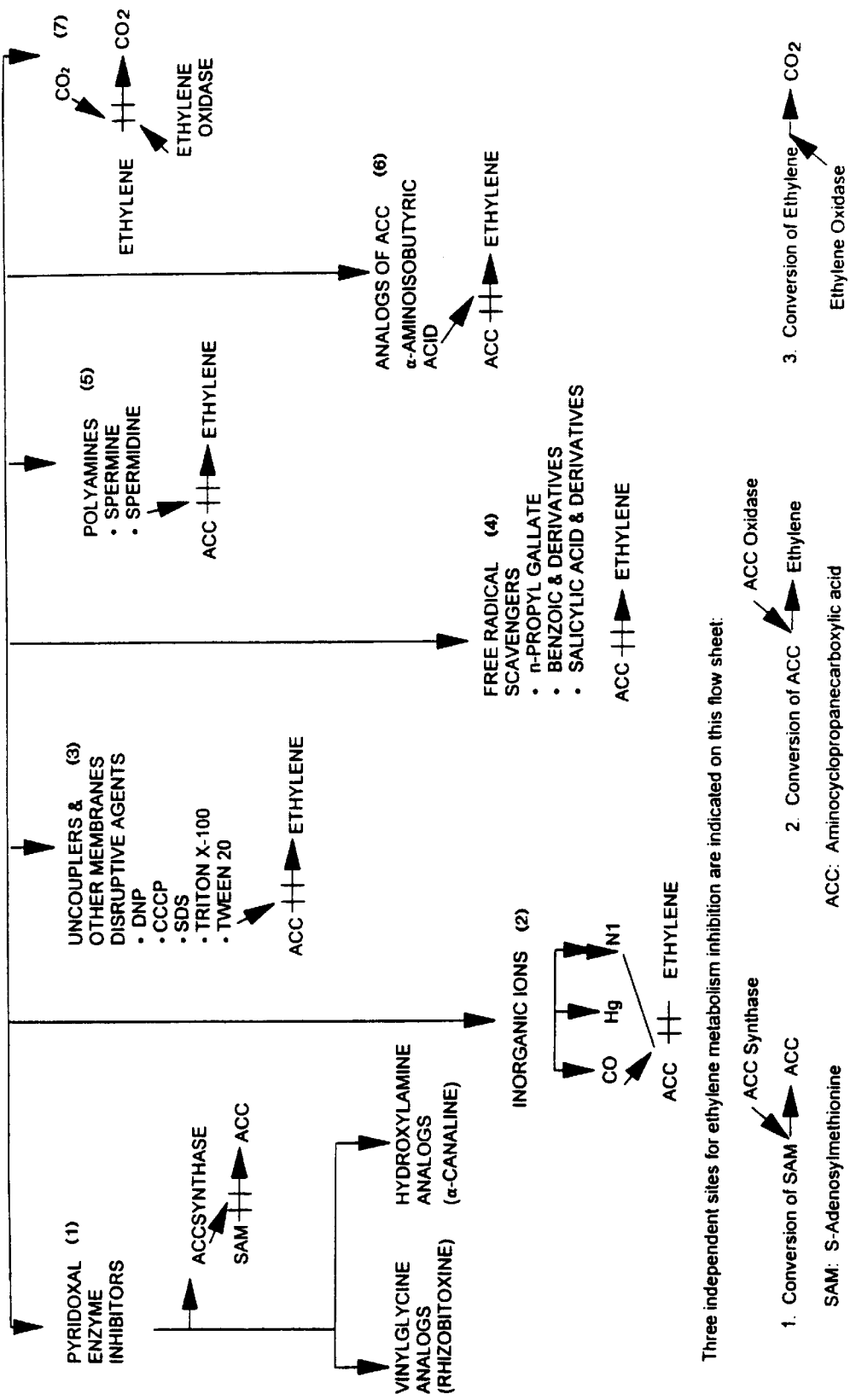
FIG. 2 Biosynthetic pathways of ethylene production and points of inhibition.

As shown in FIG. 2, there are a large number of pathways in the biosynthesis of ethylene and a equally large number of inhibitors. For example, biosynthetic pathways can be inhibited at the conversion of S-adenosyhnethionine (SAM) (ACC synthase+SAM→ACC), aminocyclopropane carboxylic acid (ACC) (ACC+ACC oxidase→ethylene), and ethylene (ethylene+ethylene oxidase→$CO_2$). A number of the biosynthetic inhibitors which can be used in the methods of the invention are shown in Table 1.

TABLE 1

| Inhibitors of Ethylene Biosynthesis | | |
|---|---|---|
| Rhizobitoxin | Methoxylamine HCl | Hydroxylamine Analogs |
| α-Canaline | DNP (2,4-dinitrophenol) | SDS (sodium lauryl sulfate) |
| Triton X-100 | Tween 20 | Spermine |
| Spermidine | ACC Analogs | α-Aminoisobutyric Acid |
| n-Propyl Gallate | Benzoic Acid | Benzoic Acid Derivatives |
| Ferulic Acid | Salicylic Acid | Salicylic Acid Derivatives |
| Sesamol | Cadavarine | Hydroquinone |
| Alar | AMO-1618 | BHA (butylated hydroxyanisol) |
| Phenylethylamine | Brassinosteroids | P-chloromercuribenzoate |

TABLE 1-continued

| Inhibitors of Ethylene Biosynthesis | | |
|---|---|---|
| N-ethylmaleimide | Iodoacetate | Cobalt Chloride and other salts |
| Bipyridyl | Amino (oxyacetic) Acid | Mercuric Chloride and other salts |
| Salicyl alcohol | Salicin | Nickle Chloride and other salts |
| Catechol | Pffloroglucinol | 1,2-Diaminopropane |
| Desferrioxamine | Indomethacin | 1,3-Diaminopropane |

There are also a large number of inhibitors of ethylene action. Some of these compounds are shown in Table 2.

TABLE 2

| Inhibitors of Ethylene Action | |
|---|---|
| Silver Salts | Benzylisothiocyanate |
| 8-Hydroxyquinoline sulfate | 8-Hydroxyquinoline citrate |
| 2,5-norbornadiene | N-ethoxycarbonyl-2-ethoxy-1,2-dihydroquinoline |
| Trans-cyclootene | 7-Bromo-5-chloro-8-hydroxyquinoline |
| Cis-Propenylphosphonic Acid | Diazocyclopentadiene |
| Methylcyclopropane | 2-Methylcyclopropane Carboxylic Acid |
| Methylcyclopropane carboxylate | Cyclooctadiene |
| Cyclooctodine | (Chloromethyl) Cyclopropane |

It has been known since 1976 that silver ions act as a potent anti-ethylene agent in various plants and for improving the longevity of plant tissues and cell cultures. For example, the longevity of cut carnations can be increased by pretreatment with silver salts. Due to the relative immobility of the silver ion, a basal treatment of the stem is considered to be less effective than a direct spray treatment of the flowers. The low mobility of silver ion is found to increase by cheating the metal to an anionic complex such as silver thiosulfate. Thiosulfate alone neither affects ethylene biosynthesis nor inhibits ethylene action.

Silver ion mediated ethylene inhibition could be explained on the basis that silver is substituted for copper on the same receptor site. it is also proposed that copper is the metal involved in enzymatic reactions related to the biosynthesis or the action of ethylene. The similarity in size of silver and copper, the same oxidation state and the ability of both metals to form complexes with ethylene lend credence to this idea.

Silver salts including silver thiosulfate inhibits ethylene action in plants and plant cell cultures even though it has a remarkable stimulatory effect on its synthesis. The stimulatory effect of silver ions (active ingredient of silver thiosulfate) on both ACC and ethylene biosynthesis suggests increased conversion of ACC to ethylene due to increased activity of ACC oxidase. Some of the silver salts that inhibit ethylene action are shown in Table 3.

TABLE 3

| Selected Silver Salts | | |
|---|---|---|
| Silver Thiosulfte | Silver Nitrate | Silver Chloride |
| Silver Acetate | Silver Phosphate | Citric Acid Tri-Silver Salt |
| Silver Benzoate | Silver Sulfate | Silver Oxide |
| Silver Nitrite | Silver Cyanate | Lactic Acid Silver Salt |

TABLE 3-continued

Selected Silver Salts

| | |
|---|---|
| Silver Pentafluoropropionate | Silver Hexafluorophosphate |
| Silver Salts of Toluenesulfonic Acid | |

Stabilizers are preferably incubated with plant cells prior to freezing, although their presence during the freezing process, recovery, thawing and regrowth, may also be desirable. For example, ethylene biosynthesis inhibitors and ethylene action inhibitors may be more desirable to have in the culture medium during thawing and regrowth. Incubations can be performed for hours or days as the agents themselves are generally not harmful to the cells and may even increase viability. Some of the more sensitive plant cell lines may require longer treatments while others shorter. The exact period of incubation can be easily determined empirically. Preferably, plant cells are cultured in growth medium with the stabilizer or a combination of stabilizers for about 1 to about 10 days, more preferably for about 1 to about 7 days and even more preferably about 3 days. This amount of time is typically sufficient for damaging substances in the medium to be eliminated or at least reduced to levels which are no longer harmful to the cells.

Incubations can be performed in liquid or semi-solid mediums such as growth medium, medium that encourages metabolism and cell proliferation, or maintenance medium, medium that provides a balance of salts and nutrients without necessarily encouraging cell growth. As the cells are being prepared for cryopreservation, it is sometimes desirable to incubate in maintenance medium (a sub-optimal or slow growth culture medium; e.g. one fourth of the salt concentration of the normal growth medium) to reduce the metabolic processes of the cells.

Pretreatment can be performed by preculturing cells at room temperature or at temperatures which the plant cells are typically cultured. Preferably, preculturing is performed at about room temperature (20° C.) for ease of handling and as most plant cells are fairly stable at room temperature. Stabilizers can be added directly to the medium and replenished as necessary during the pretreatment process. Stabilizer concentrations are particular to specific stabilizers, but are generally used at between about 1 $\mu$M to about 1 mM, or preferably at between about 10 $\mu$M to about 100 $\mu$M, although more or less of one or more stabilizing agents would not be uncommon.

Pretreatments may also involve incubating cells in the presence of one or more osmotic agents. Examples of useful osmotic agents include sugars such as saccharides and saccharide derivatives, amino or imino acids such as proline and proline derivatives, or combinations of these agents. Some of the more useful sugars and sugar derivatives are fructose, glucose, maltose, mannitol, sorbitol, sucrose and trehalose. Osmotic agents are utilized at a concentration that prepares cells for subsequent loading, lyophilization and/or vitrification. Concentrations can vary greatly between different agents, but are generally between about 50 mM to about 2 M. These concentrations can be achieved by adding small amounts of the agents continuously or incrementally over time (stepwise) until a desired level is achieved. Preferably, osmotic agents concentration in media are between about 0.1 M to about 0.8 M, and more preferably at between about 0.2 M to about 0.6 M. Alternatively, the osmotic agent is employed as an aqueous solution at a concentration of between about 1% to about 10%, by weight.

Pretreatment may also simply involve the addition of membrane stabilizers such as compounds that intercalate into the lipid bilayer (e.g. sterols, phospholipids, glycolipids, glycoproteins) or divalent cations into the cell culture, the loading solution and/or the vitrification solution. Divalent cations stabilize heat shock and membrane proteins, and also reduce electrostatic repulsion between cellular and other membranes. Magnesium, manganese and calcium are preferred choices as inexpensive and readily available divalent cations in the form of, for example, $CaCl_2$, $MnCl_2$ and $MgCl_2$. Sodium is less preferred due to its toxicity at any more than trace concentrations. Preferred concentrations range from about 1 mM to about 30 mM, and more preferably from about 5 mM to about 20 mM and still more preferably at about 10 mM or 15 mM. In addition, the presence of divalent cations in the medium reduces freezing temperatures and allows for the more rapid passage of cells through freezing points. The temperature of both intercellular and intracellular ice crystal formation is reduced upon freezing and also during thawing. The presence of these agents during thawing and post-thawing culture can also be important.

Cold Acclimation

During or at some time after pretreatment, cells to be cryopreserved may be acclimated to a temperature which is reduced from culturing temperatures, but above freezing. This prepares cells for the cryopreservation process by significantly retarding cellular metabolism and reducing the shock of rapid temperature transitions through some of the more critical temperature changes. Critical temperature ranges are those ranges at which there is the highest risk of cell damage, for example, around the critical temperatures of ice crystal formation. As known to those of ordinary skill in the art, these temperatures vary somewhat depending upon the composition of the solution. For water, the principal component of most cell culture mediums, ice crystal formation and reformation occur at about 0° C. to about –50° C.

Acclimation results in the accumulation of endogenous solutes that decreases the extent of cell dehydration at any given osmatic potential, and contributes to the stabilization of proteins and membranes during extreme dehydration. In addition, cold adaptation interacts synergistically with the vitrifying agents and results in alterations in the liquid conformation of the cellular membranes, that increase tolerance to both osmotic exclusions and dehydration.

Acclimation may be carried out in a stepwise fashion or gradually. Steps may be in decreasing increments of about 0.5° C. to about 10° C. for a period of time sufficient to allow the cells acclimate to the lower temperature without causing damage. The temperature gradient, whether gradual or stepwise, is scaled to have cells pass through freezing points as quickly as possible. Cells may be gradually, in a step-wise or continuous manner, or rapidly acclimated to the reduced temperature. Techniques for acclimation are well known to those of ordinary skill and include commercially available acclimators. Gradual acclimation comprises reducing incubation temperatures about 1° C. per hour until the target temperature is achieved. Gradual acclimation is most useful for those cells considered to be most sensitive and difficult to cryopreserve. Stepwise acclimation comprises placing the cells in a reduced temperature for a period of time, a further reduced temperature for another period of time. These steps are repeated as required.

Suspension cells can be in late lag or early cell division phases to achieve the greatest survival rates on freezing and thawing. Cells beyond these phases exhibit higher degrees of vacuolation and differentiation and are larger in size, thus enhancing the risk of freezing injury and decreasing survival rates on freezing and thawing.

Loading

Loading involves the equilibration of cells in a solution of one or more cryoprotectants. Agents utilized during loading may be referred to as loading agents. Useful loading agents may include one or more dehydrating agents, permeating and non-permeating agents, and osmotic agents. Suitable agents for loading include agents which induce cell dehydration upon introduction to a cell suspension. Both permeating agents such as DMSO and ethylene glycol, and a combination of permeating and nonpermeating osmotic agents such as fructose, sucrose or glucose, and sorbitol, mannitol or glycerol can be used. This step increases solute concentration of the cytosol by introducing moderate concentrations of cryoprotective agents, generally at between about 0.5 M to about 2 M or between about 5% to about 20%, by weight, into the cytosol. To minimize the time required for equilibration, loading is usually performed at about room temperature, although optimal temperature and other conditions for loading will preferably match conditions such as medium, light intensities and oxygen levels that maintain a viable cell culture.

In the loading step, single cryoprotective agents or combinations of different cryoprotective agents can be added directly to the incubation medium continuously or in a stepwise fashion. Stepwise loading is sometimes desired to facilitate delivery of the loading agent to cells as it is somewhat more gentle than single dose loading. Time increments or interval between additions for stepwise loading may range from minutes to hours or more, but are preferable from about one to about ten minutes, more preferably from about one to about five minutes and still more preferably about one or about two minute intervals. The numbers of additions in a stepwise loading procedure is typically whatever is practical and can range from very few to a large plurality. Preferably, there are less than about twenty additions, more preferably less than about ten and even more preferably about five. Interval periods and numbers of intervals are easily determined by one of ordinary skill in the art for a particular type of cell and loading agent. Cells are incubated in a solution containing the loading agent or agents (with continuously or stepwise increasing amounts of loading agent) to equilibrate intracellular and/or extracellular concentrations of the agent. Incubation times range from minutes to hours as practical. The protective effects of loading include, in part, removal of a small, but significant amount of water from the cell. This prepares the cell for subsequent vitrification and/or lyophilization by minimizing the shock of sudden intracellular water loss.

After loading, growth medium containing the cryoprotective agent can be removed or, if the following agent (vitrifying agent) to be utilized is the same or a similar agent, the loading agent can remain and the concentration simply increased for vitrification.

Vitrification

Cells to be cryopreserved are vitrified following pretreatment, loading and/or lyophilization. There are several advantages of the verification procedures. By precluding ice crystal formation in the system, the need to optimize the complex set of variables which lead to ice formation is eliminated. Further, specimens can be plunged directly in liquid nitrogen, the procedure does not require extensive equipment required for controlled cooling. The vitrification procedure also offers the greatest potential for developing cryopreservation procedures for complex tissues and organs that are comprised of several different types of cells.

Vitrification procedures involve gradual or stepwise osmotic dehydration of the cells or specimens prior to quenching in liquid nitrogen. In vitrification procedures, cell dehydration is effected by direct exposure to concentrated solutions prior to cooling in liquid nitrogen. Exposure can be gradual with continuously increasing amounts of the vitrification added to the cells or stepwise wherein increasing amounts are added over a set period of time. Time increments or interval between additions for stepwise vitrification may range from minutes to hours or more, but are preferable from about one to about ten minutes, more preferably from about one to about five minutes and more preferably about one or about two minutes. The numbers of additions in a stepwise vitrification procedure is typically whatever is practical and can range from very few to a large plurality. Preferably, there are less than about twenty additions, more preferably less than about ten and even more preferably about five. Interval periods and numbers of intervals are easily determined by one of ordinary skill in the art for a particular type of cell and vitrification agent. Cells are incubated in a solution containing the vitrification agent or agents (with continuously or stepwise increasing amounts) to equilibrate intracellular and/or extracellular concentrations of the agent as desired. Incubation times vary from minutes to hours as practical. Under ideal conditions the cells or organs can be cooled at extremely rapid rates without undergoing intercellular or intracellular ice formation. As a result, all of the factors that affect ice formation are obviated and there are several practical advantages of the vitrification procedures in comparison to conventional cryopreservation procedures. Vitrification offers the greater potential for developing cryopreservation procedures for complex tissues and organs. By precluding significant ice formation in the system, the vitrification procedure is operationally more complex than conventional cryopreservation procedures. Further, vitrification allows for the use of ultra-rapid cooling rates to circumvent problems of chilling sensitivity of some specimens. No specialized or expensive equipment is required for controlled cooling rates.

Vitrification is a cryogenic method wherein a highly-concentrated cytosol is super-cooled to form a solid, meta-stable glass without substantial crystallization. The major difficulty in cryopreservation of any cell is the formation of intracellular ice crystals during both freezing and thawing. Excessive ice crystal formation will lead to cell death due to disruption of cellular membranes and organelles. One method to prevent ice crystal formation is to freeze the cells rapidly such that the ice crystals formed are not large enough to cause significant damage. When a cell with a low water content is frozen rapidly, it vitrifies. Vitrification by rapid freezing is not possible with cells such as plant cells which containing a high water content. To vitrify high water content cells, freezing point reduction agents and ice crystal inhibitors is needed in addition to rapid freezing for vitrification. A properly vitrified cell form a transparent frozen amorphous solid consisting of ice crystals too small to diffract light. If a vitrified cell is allowed to warm to about $-40°$ C., it may undergo devitrification. In devitrification, ice crystals enlarge and consolidate in a process which is generally detrimental to cell survival. Vitrification solutions enhance vitrification of cells upon freezing or retard devitrification upon thawing.

Most cryopreservation solutions can transform the subject material into a glass or glass-like material provided cooling rates are sufficiently rapid to prevent the nucleation and growth of ice crystals, with the critical cooling rate dependent on the solute concentration. Similarly, vitrification of the cells can be effected if the cytosol is sufficiently concentrated. In cryopreservation procedures, this is achieved by dehydrating the cells in extremely concentrated solutions prior to quenching in liquid nitrogen. In the cryopreservation process, the cytosol is concentrated to the level required for vitrification by placing the specimens in a concentrated solution of a cryoprotective such as the vitrifying agent. Concentrations such as about 4 M to about 10 M, or between about 25% to about 60%, by weight, are preferred. This produces an extreme dehydration of the sample cells. Solutions in excess of 7 M typically remove more than 90% of the osmotically active water from the cells; however, precise concentrations for each agent can be empirically determined. Vitrifying agents which may be used include DMSO, propylene glycol, glycerol, polyethylene glycol, ethylene glycol, butanediol, formamide, propanediol and mixtures of these substances.

Suitable vitrification solutions include culture medium with DMSO (1–50%), propylene glycol (about 5–25%), glycerol (about 0–50%), PEG-8000 (about 5–20%), ethylene glycol (about 10–75%), ethylene glycol/sorbitol (about 60/20 weight percent to about 10/60 weight percent), and ethylene glycol/sorbitol (about 40/30 weight percent). Ethylene glycol/sorbitol is preferred and can be employed at concentrations of, for example, 50/30%, 45/35%, 40/40%, 40/30%, 30/50 and, preferably, 30/40%. Such vitrification solutions can be utilized at temperatures from about 1° C. to about 8° C., preferably at a temperature of from 2° C. to 6° C., and more preferably at about 4° C.

To minimize the injurious consequences of exposure to vitrification solutions, dehydration may be performed at about 0° C. to about 4° C., with the time of exposure as brief as possible. Under these conditions, there is no appreciable influx of additional cryopreservation into the specimens because of the difference in the permeability coefficient for water and solutes. As a result, the specimens remain contracted and the increase in cytolic concentration required for vitrification is attained by dehydration. However, equilibrium (loading) of the cells with cryoprotectants is not always required for successful vitrification of plant cells or organs. For example, in some cases, preculturing with loading agents achieve the same purposes as the loading step.

In those instances in which loading is required, it primarily serves to prevent dehydration-induced destabilization of cellular membranes and possibly proteins. However, in the absence of a loading step, there can be less survival of cells following the dehydration and cooling/warming steps. Thus, intracellular ethylene glycol or other cryoprotectants during the loading step not only favors vitrification of the cells during cooling, but also protects cells against injury during the dehydration step.

Lyophilization

Lyophilization is directed to reducing the water content of the cells before cryopreservation by vacuum evaporation. Vacuum evaporation involves placing the cells in an environment with reduced air pressure. Depending on the rate of water removal desired, the reduced ambient pressure operating at temperatures of between about −30° C. to −50° C. may be at 100 torr, 1 torr, 0.01 torr or less. Under conditions of reduced pressure, the rate of water evaporation is increased such that up to 65% of the water in a cell can be removed overnight. With optimal conditions, water removal can be accomplished in a few hours or less. Heat loss during evaporation maintains the cells in a chilled state. By careful adjustment of the vacuum level, the cells may be maintained at a cold acclimation temperature during the vacuum evaporation process. A strong vacuum, while allowing rapid water removal exposes the cells to the danger of freezing. Freezing may be controlled by applying heat to the cells directly or by adjustment of the vacuum level. When the cells are initially placed in the evaporative chamber, a high vacuum may be applied because the residue heat in the cells will prevent freezing. As dehydration proceeds and the cell temperature drops, the vacuum may be decreased or heating may be applied to prevent freezing. The semi-dry cells may have a tendency to scatter in an evaporative chamber. This tendency is especially high at the end of the treatment when an airstream is allowed back into the chamber. If the air stream proximates the semi-dry cells, it may cause the cells to become airborne and cause cross contamination of the samples. To prevent such disruptions, evaporative cooling may be performed in a vacuum centrifuge wherein the cells are confined to a tube by centrifugal force while drying. The amount of water removed in the process may be monitored periodically by taking dry weight measurement of the cells. When the desired amount of water is removed, vitrification solution may be added directly to the semi-dry cells for a period to time prior to direct freezing in liquid nitrogen.

Freezing

Plant cells, which may have been pretreated, loaded, vitrified and/or lyophilized, are preserved by freezing to cryopreservation temperatures. The freezing step should be sufficiently rapid to prevent the formation of large ice crystals which are detrimental to the cell's survival. Cells may be directly frozen, that is brought directly into contact with an agent already at cryopreservation temperature. Direct methods include dripping, spraying, injecting or pouring cells directly into a cryogenic temperature fluid such as liquid nitrogen or liquid helium. Cells may also be directly contacted to a chilled solid, such as a liquid nitrogen frozen steel block. The cryogenic fluid may also be poured directly onto a container of cells. The direct method also encompasses contacting cells with gases, including air, at a cryogenic temperature. A cryogenic gas stream of nitrogen or helium, may be blown directly over or bubbled into a cell suspension. Indirect methods involve placing the cells in a container and contacting the container with a solid, liquid, or gas at cryogenic temperature. Proper containers include, for example, plastic vials, glass vials or ampules which are designed to withstand cryogenic temperatures. Containers for indirect freezing methods do not have to be impermeable to air or liquid. For example, a plastic bag or aluminum foil are adequate. Furthermore, the container may not necessarily be able to withstand cryogenic temperatures. A plastic vial which cracks, but remain substantially intact under cryogenic temperatures may also be used. Cells may also be frozen by placing a sample of cells on one side of a metal foil while contacting the other side of the foil with a gas, solid, or liquid at cryogenic temperature. Freezing should be sufficiently rapid to inhibit ice crystal formation. The freezing time should be around 5 minutes or 4 minutes, 3 minutes, 2 minutes, or one minute or less. The critical freezing time should be measure from the frame of reference of a single cell. For example, it may take 10 minutes to pour a large sample of cells into liquid nitrogen, however the individual cell is frozen rapidly by this method.

Thawing

Another embodiment of the invention is directed to methods for thawing cryopreserved cells. Proper thawing and recovery is essential to cell survival and to recovery of cells in a condition substantially the same as the condition in which they were originally frozen. As the temperature of the cryopreserved cells is increased during thawing, small ice crystals consolidate and increase in size in a process termed devitrification. Large intracellular ice crystals are generally detrimental to cell survival. To prevent devitrification, cryopreserved cells should be thawed as rapidly as possible. The rate of heating may be at least about 30° C. per minute to 60° C. per minute. More rapid heating rates of 90° C. per minute, 140° C. per minute to 200° C. or more per minute can also be used. While rapid heating is desired, plant cells have reduced ability to survive incubation temperature significantly above room temperature. To prevent overheating, the cell temperature should be carefully monitored. Any heating method can be employed including conduction, convection, radiation, electromagnetic radiations or combinations thereof. Conduction methods involve immersion in water baths, placement in heat blocks or direct placement in open flame. Convection methods involve the use of a heat gun or an oven. Radiation methods involve, for example, heat lamps or ovens such as convection or radiation ovens. Electromagnetic radiation involves the use of microwave ovens and similar devices. Some devices may heat by a combination of methods. For example, an oven heats by convection and by radiation. Heating should be terminated as soon as the cells and the surrounding solutions are in liquid form, which should be above 0° C. Cryopreserved cells are often frozen in the presence of one or more agents that depress the freezing point. When these agents are present, the frozen cells may liquify at a temperature below 0° C. such as at about –10° C., –20° C., –30° C. or –40° C. Thawing of the cryopreserved cells may be terminated at any of these temperature or at a temperature above 0° C.

Post-Thawing

Dilution of the vitrification solution and removal of cryopreservative from the cells, referred to as unloading, should be performed as rapidly as possible and as quickly as possible subsequent to thawing of the cryopreserved cell sample. Due to the high intracellular concentrations of cryopreservative, it is preferred to effect the dilution of the suspending medium while minimizing osmotic expansion. Therefore, dilution of the suspending medium and efflux of the cryopreservative from within the sample specimen is usually accomplished by dilution in an hypertonic medium or a step-wise dilution.

Thawed cells can be gradually acclimated to growth conditions to maximize survival. Vitrification agents may be cytotoxic, cytostatic or mutagenic, and should be removed from the thawed cells at a rate which would not harm the cells. A number of removal methods may be used such as resuspension and centrifugation, dialysis, serial washing, bioremediation and neutralization with chemicals, or electromagnetic radiation. The rapid removal of some vitrification solutions and osmotic agents may increase cell stress and death and thus the removal step may have to be gradual. Removal rates may be controlled by serial washing with solutions that contain less osmotic or vitrification agents. Other method to reduce the removal rate include dialysis with less permeable membranes, serial growth on semisolid or liquid media containing less and less concentration of vitrification agents. Other methods include gradual dilutions, dialysis, bioremediation, neutralization and catalytic breakdown of the cryogenic agent.

Thawing and post-thaw treatments may be performed in the presence of stabilizers to ensure survival and minimize genetic and cellular damage. The stabilizer such as, for example, divalent cations or ethylene inhibitors, reduce, eliminate or neutralize damaging agents which results from cryopreservation. Such damaging agents include free radicals, oxidizers and ethylene. Some of these agents have multiple properties and are very useful in this regard. Survival and regrowth rates are surprisingly enhanced with the addition of stabilizers during the thawing and post thawing steps.

Cells can be regrown in suitable media after levels of osmotic or vitrification agents are reduced to an acceptable level. One method for regrowth involves placing the thawed cells in semisolid growth media, such as agar plates, until a callus is formed. Cells may be recovered from the callus and grown in liquid culture. Alternatively, callus cells may be induced to grow shoots and roots by placement in semisolid media containing the appropriate hormones. Callus cells with shoots and roots may be gradually acclimated to grow on sterile soil in a greenhouse until a plant develops. The greenhouse plant may be acclimated to grown outside a greenhouse in its natural environment. Alternatively, a cell may be thawed and regrown without the use of semi-solid media. That is, after removal of osmotic and vitrification agents, the cells may be placed directly into liquid media for regrowth.

Inclusion of one or more of the variations disclosed herein can substantially increase cell recovery after cryopreservation for a variety of cell types. These methods prevent problems associated with toxicity due to cryoprotectants, build-up of ethylene, ethylene action on specific targets including the membrane associated receptors, instability of membranes and membrane leakage. From the methods disclosed herein, particular combinations of steps have been identified as optimal for certain cell types. For example, tomato, potato and tobacco cells respond well to cryopreservation using stepwise loading and/or vitrification with divalent cations (Protocols 10, 12, 13, 14).

Figure 3:
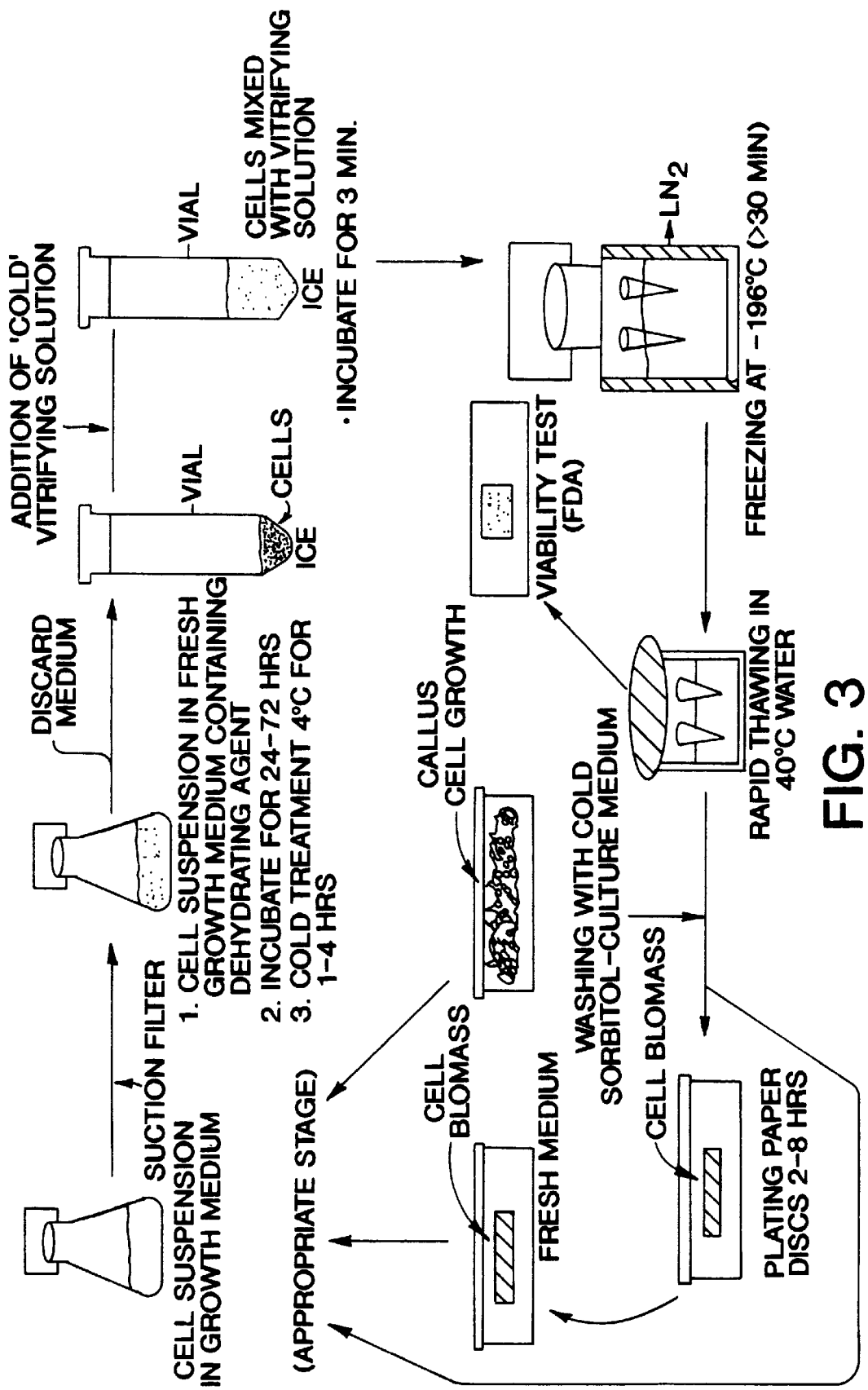
FIG. 3 Procedure for cryopreservation of Taxus cells.

One method to implement cryopreservation of plant cells, for example, taxol producing Taxus cells, is schematically represented in FIG. 3. Briefly, a callus cell growth from a primary isolate or from a cell culture is adapted for culture in liquid growth medium. After the cells have adjusted to liquid culture, they are transferred to a pretreatment growth medium containing an osmotic agent and a stabilizer for 24 to 72 hours. Precultured cells are subsequently cold acclimated by the incubation of the pretreatment culture at 4° C. for 1 to 4 hours. After cold acclimation, cells are transferred to a centrifuge vial and subjected to mild centrifugation which pellets the cells without damage. Supernatant, comprising the pretreatment media with osmotic agents and the stabilizer, is aspirated from the cell pellet and discarded. A prechilled solution, comprising a stabilizer and a vitrification agent, is added to the cell pellet and the cells are gently resuspended. After 3 minutes of treatment with the vitrification solution, the cells are placed into archival cryogenic storage by immersion of the vial containing the cells in liquid nitrogen. Cryogenically preserved cells are stored in liquid nitrogen for a period from about 30 minutes to many years. To revive the cells, the vial containing the cryopreserved cells is rapidly transferred from liquid nitrogen to a 40° C. water bath. The vial is removed from the 40° C. bath when the contents are liquified. An aliquot of the thawed cells is inspected for immediate viability by dye exclusion analysis. The remaining cells are washed by a series of cold growth medium containing a stabilizer and a progressively lower concentrations of osmotic agents. After sufficient osmotic and vitrification agents are removed from the cells by serial washes, the cells are transferred directly into liquid culture. Alternatively, cells are placed on a plating paper and transferred to a series of semi-solid medium with a stabilizer and a decreasing amount of osmotic and vitrification agents. This serial plating is continued until the cells have adjusted to growth on semi-solid medium in the absence of osmotic and vitrification solutions.

Other methods of cell cryopreservation are disclosed in FIGS. 1A, 1B and 1C. As can be see in this schematic representation, a number of variations are preferred. For example, in step 1, cell biomass is precultured in liquid medium containing osmotic agent (sucrose, sorbitol or mannitol with concentration ranges from 0.06 M to 0.80 M) for 1 to 6 days in liquid medium. In step 2, loading is performed stepwise. Precultured cell biomass is loaded with cryoprotectants (20% of vitrification solution (V2N) containing ethylene glycol/sorbitol at a concentration of 40/30 weight percent in nutrient culture medium or 20% of vitrification solution (VS3) containing 30% (w/v) glycerol, 15% (w/v) ethylene glycol and 15% (w/v) dimethylsulfoxide in nutrient culture medium or in 0.4M sucrose solution (pH 5.6 to 5.8). Cell biomass in liquid is mixed gently and incubated on ice or in refrigerate at 0° C. to 4° C. for five minutes. Immediately after this step, the concentration of cryoprotectants in liquid is increased stepwise by adding five times chilled 100% vitrification (V2N or VS3) solution at one minute intervals until the final concentration of vitrification solution is reached at 65%. The total time used for this loading step and incubation at 0° to 4° C. is ten minutes. The mixture (cell biomass+vitrification) is centrifuged for up to five minutes (one to five minutes) at 100× g and the supernant is discarded.

Alternatively, in step 2, loading can be performed in a single step. Precultured cell biomass is loaded with cryoprotectants (65% of a vitrification solution—V2N containing ethylene glycol/sorbitol at a concentration of 40/30 weight percent in nutrient culture medium; or 65% of a vitrification solution—VN3 containing 30% (w/v) glycerol, 15% (w/v) ethylene glycol and 15% (w/v) DMSO in nutrient culture medium; or in 0.4 M sucrose solution (pH 5.6–5.8)). Cell biomass in liquid containing cryoprotectants is mixed gently and incubated on ice or refrigerated at 0° C. to 4° C. for ten minutes.

Alternatively, loading can be performed stepwise or in one step with cryoprotectants containing one or more membrane stabilizers. All biological membranes have a common overall structure. They are assemblies of lipid and protein molecules held together by noncovalent interactions. Lipids are arranged as a bilayer, which provides the basic structure of the membrane and serves as a relatively impermeable barrier to the flow of most water-soluble molecules. Protein molecules are within the lipid bilayer and modulate the various functions of the membrane. Some service to transport specific molecules into or out of the cell such as, for example, channel proteins such as passive channel proteins, carrier proteins and proteins involved in active transport. Others are enzymes that catalyze membrane-associated reactions, and still others serve as structural links between the cell's cytoskeleton and extracellular matrix, and/or as receptors for receiving transducing chemical signals from the cell's environment.

Certain plant species and cell lines are recalcitrant to previously established cryopreservation protocols, partly due to their sensitivity to the type and concentration of cryoprotectants. There are at least two potential causes of membrane destabilization, chemical toxicity of the cryoprotectants used in the loading and dehydration steps and extreme dehydration resulting from exposure to the concentrated solutions (e.g. vitrification). Other factors such as the ice formation during either cooling or warming, and mechanical disruption of cells due to fracturing of the glass can also contribute to destabilization of membranes.

Severe dehydration resulting from the exposure to concentrated solutions of cryoprotectants can cause the structural transitions in a diverse array of biological molecules including lipids, proteins and nucleic acids. Under these conditions, there are several alterations in the ultrastructure of the plasma membrane and other cellular membranes. These changes include the formation of a particulate domains in the plasma membrane which result in the removal of water that is associated with the hydrophilic regions of the proteins and lipid components of the membranes. Alternatively, destabilization can also occur by contacting plant cell membranes with a permeablizing cryoprotectant compound (i.e. a compound that fluidizes a channel protein within a plant cell membrane). Stepwise loading and/or vitrification can minimize membrane destabilization resulting from severe dehydration. Other features related to the substantial changes in cell volume, permeability of the plasma membrane, etc. can also be minimized by stepwise loading.

Heat-shock treatment will also stabilize membranes and proteins. Heat-shock treatment, after preculturing cell biomass with osmotic agents, is not necessary prior to loading cells with cryoprotectants. However, heat-shock treatment is required when the cell biomass is not precultured with osmotic agents. Furthermore, it is important to load cells with vitrifying solution (cryoprotectants) containing divalent cation ($CaCl_2$, $MnCl_2$ or $MgCl_2$; at 5 mM to 20 mM) (e.g. Protocols 11 and 12). Heat-shock treatment is usually followed after preculturing of cell biomass. It tends to improve the survival of cells after cryopreservation by about 20% to about 40%. This procedure involves the incubation of cells or cell biomass (either precultured or non-precultured) in a water-bath shaker at about 37° C. for up to about four hours. After this treatment, cells in liquid medium (with or without osmotic agent) are transferred to room temperature (23° C. to 25° C.) for up to four hours before being used for cryopreservation (loading step).

Heat-shock treatment is known to induce de novo synthesis of certain proteins (heat-shock proteins) that are supposed to be involved in adaptation to stress. Heat-shocked cells that are not precultured with osmotic agent do not survive freezing. Heat shock induces tolerance to exposure by abruptly increasing the concentration of osmotics in cells that result from freezing by the formation of heat-shock proteins that stabilize proteins and membranes. Heat shock is performed by culturing the cells in a water bath at between about 31° C. to about 45° C., preferably between about 33° C. to about 40° C. and more preferably at about 37° C. Culturing is performed from a few minutes to a few hours, preferably from about one hour to about six hours, and more preferably from about two hours to about four hours.

Divalent cations such as $CaCl_2$, $MnCl_2$ or $MgCl_2$, can also be included in a vitrifying solution prior to the exposure of cells to $LN_2$ temperatures. Divalent cations included in the vitrifying solutions appear to stabilize plant cell membranes and heat-shock proteins. Divalent cations stabilize cell membranes by reducing electrostatic repulsion between ionic centers on the membrane. Additionally, divalent cations can also prevent ice nucleation during freezing and thawing. Other compound such as sterols, phospholipids, glycolipids or glycoproteins which intercalate into the lipid bilayer of membranes, may also effectively stabilize plant cell membranes. These compounds may be substituted for divalent cations in stabilization of plant cell membranes and/or heat-shock proteins.

The procedure for stepwise loading precultured or non-precultured cell biomass (with or without heat-shock treatment at 37° C. up to four hours) with cryoprotectants is the same as before except the vitrifying solutions (V2N or VS3) contained the membrane stabilizer divalent cations (e.g. $CaCl_2$, $MnCl_2$, $MgCl_2$) at a concentration ranging from 5 mM to 20 mM.

In step 3, the vitrification step can be stepwise. Cells or cell biomass thus obtained after loading and centrifugation are further treated with vitrifying solution (V2N or VS3) in a stepwise manner. This step usually involves the transfer of cell biomass after centrifugation to a chilled cryovial, and adding a concentrated (100%) vitrification solution at one minute intervals during the three minute incubation period at 0° C. At the end of incubation period, the contents (cells+vitrifying solution) in a cryovial are mixed gently prior to a plunge into $LN_2$. Alternatively, vitrification can be performed in a single step. Cells or cell biomass thus obtained after loading and centrifugation are further treated with vitrification solution (100%). This step usually involves the transfer of cell biomass after centrifugation to a chilled cryovial, and adding a concentrated (100%) vitrifying solution. The contents in a cryovial are mixed gently and are incubated for three minutes at 0° C. prior to a plunge into $LN_2$. Alternatively still, vitrification can be stepwise or one step with cryoprotectants containing divalent cation such as $CaCl_2$ or $MgCl_2$.

The procedure for vitrification of loaded cell biomass with cryoprotectants is the same as before except the concentrated vitrifying solution (V2N or VS3) contained the membrane stabilizer divalent cations ($CaCl_2$ or $MgCl_2$) at a concentration ranging from about 5 mM to about 20 mM.

Freezing of cells is generally rapid in cryovials in $LN_2$ or the rapid transfer of cryovials containing cells in vitrification solution to a storage vessel containing liquid nitrogen ($LN_2$).

Thawing involves a rapid warming (e.g. about 20 seconds to about 45 seconds) of cryovials containing frozen cell biomass or cells in a water bath set at 40° C. or 60° C. Post-thawing involves the immediate transfer of liquefied cell biomass in cryovials to a sterile centrifuge tube containing liquid nutrient medium with an osmotic agent (sucrose, sorbitol or mannitol; concentration range 1M to 2M) and an ethylene inhibitor or ethylene action inhibitor (silver thiosulfate; concentration range from about 5 $\mu$M to about 20 $\mu$M). Contents are mixed gently and incubated on a shaker (120 rpm) for 30 minutes at room temperature. This is followed by centrifugation and transferring the cells in a pellet to two layers of sterile filter paper placed on a blotting paper (to aid in removal of excessive moisture from cells or cell biomass). Cells or cell biomass was incubated for two minutes. After this incubation period, the upper filter paper with cells is transferred sequentially to solid nutrient medium containing osmotic agent at a decreased concentration from 0.8M to 0.1M sucrose (to bring about the osmotic adjustment of cells). At each step, cells on a filter paper are incubated for ½ hour to 1 hour and finally transferred to a normal solid nutrient medium without the presence of any additional osmotic agent. This step (without any additional osmotic agent in a normal nutrient medium) of incubation is repeated after 24 hour incubation in the dark at 25° C.

Alternatively, post-thawing of cells in a pellet upon thawing can be washed quickly with a liquid medium containing an osmotic agent (sucrose, sorbitol or mannitol; concentration range: 1M to 2M). This is usually done by incubation of cell biomass for two to five minutes in liquid nutrient medium containing osmotic agent and centrifugation at 100× g for one to three minutes. This step is repeated once more prior to the incubation of cell biomass for 30 minutes in liquid nutrient medium containing osmotic agent and ethylene inhibitor or ethylene action inhibitor (silver thiosulfate at 5 $\mu$M to 20 $\mu$M).

New callus regrowth is usually visible after one week. When the new cell biomass growth is increased, callus cells are removed from the filter paper and transferred directly onto a normal solid nutrient medium. After sufficient growth (usually two to three weeks) has taken place, a cell suspension in liquid medium is initiated from established callus.

Another embodiment of the invention is directed to plant cells which have been cryopreserved by the methods described above. Cells may be of any genus or species disclosed or which the cryopreservation methods can be applied. Cryopreserved cells may be maintained at temperatures appropriate for cryo-storage. Preferably, cells are maintained in liquid nitrogen (about –196° C.), liquid argon, liquid helium or liquid hydrogen. These temperatures will be most appropriate for long term storage of cells, and further, temperature variations can be minimized. Long term storage may be for months and preferably for many years without significant loss of cell viability upon recovery. As the invention also relates to efficient methods for recovery of cryopreserved cells, relatively large portions of cell samples may be lost without loss of the entire sample. Cells or plants can be propagated from those cells that remain. Short term storage, storage for less than a few months, may also be desired wherein storage temperatures of –150° C., –100° C. or even –50° C. may be used. Dry ice (carbon dioxide) and commercial freezers may be used to maintain such temperatures.

Another embodiment of the invention is directed to plants and plant cells which have been revived by the cryopreservation recovery methods described above. These cells may also be of any of the genus or species disclosed herein or a genus or species to which the methods of cryo-recovery have been applied. Cells may be the original cells which were cryopreserved or cells which have proliferated from such cells. A plant, as distinguished from a homogeneous cell culture, is a diverse collection of connected cells that possess interrelated functions.

Another embodiment of the invention is directed to methods and kits for the transportation and thawing of cryopreserved cells. Cells cryopreserved by this method may be stored in a central repository for subsequent retrieval. For increased safety against accidental loss, each cell line frozen may be stored in a number of locations. During retrieval, a cryovial containing the cryopreserved cells may be shipped in a suitable container to the recipient. Suitable container are those which can maintain cryopreservation temperature during shipment. All cells can be shipped at temperatures sufficiently low for long term storage with portable cryopreservation agents such as liquid nitrogen. Cells destined for immediate thawing may be shipped in dry ice to reduce cost. A kit for the retrieval of cells from a repository may include a vial of cryopreserved cells, sufficient media with the appropriate concentrations of osmotic agents, vitrification solutions, and stabilizers for serial washes. Alternatively, in place or in addition to the wash solution, the cells may be shipped with a plurality of semisolid growth media comprising a stabilizer and decreasing amounts of osmotic and vitrification solutions. After thawing, the cells are either washed and used immediately or they may be placed on the semisolid media to gradually remove the vitrification and osmotic agents. The transport kit may further include reagents for an post thaw viability assay and a reference DNA sample for comparison with DNA from the thawed cells to determine genetic stability.

The following experiments are offered to illustrate embodiments of the invention and should not be viewed as limiting the scope of the invention.

EXAMPLES

Example 1

Callus Initiation and Proliferation

Taxus needles were collected from wild and cultivated plants. Plant material was washed in a diluted soap solution, rinsed extensively with distilled water and surface sterilized in a chlorous solution (1% hypochlorite, pH 7) for 10 minutes. Under sterile conditions, the material was rinsed 3 times with sterile distilled water. Needles were cut in a 1% polyvinylpyrrolidone (PVP) solution with 100 mg/L ascorbic acid. Needles were placed with the cut end in semisolid medium E and incubated at 24° C.±1° C. in the dark. Cultures were monitored daily and those with signs of contaminating microorganisms were discarded. Substantial callus formation was observed and the callus was separated from the explant by 20 days and placed on the various callus proliferation media listed in Table 4. Calli of *Taxus chinensis* were transferred to medium D (Table 4). This procedure resulted in callus induction in over 90% of the explants. The same procedure was successfully used to initiate cultures of *T. brevifolia, T. canadensis, T. cuspidata, T. baccata, T. globosa, T. floridana, T. wallichiana, T. media* and *T. chinensis*. Calli removed from the explant were cultivated at 24° C. in the dark. Healthy parts of the callus were transferred to fresh medium every 10 days. The preferred growth and maintenance media for the invention are listed:

TABLE 4

Chemical Composition of Various Growth Medium

| Chemical Ingredient | A | B | C | D | E | F | G | H |
|---|---|---|---|---|---|---|---|---|
| Ammonium Nitrate | — | — | — | — | — | 400 | 500 | 400 |
| Ammonium Sulfate | 134 | — | 33.5 | 134 | 67 | — | 134 | — |
| Boric Acid | 3 | 1.5 | 0.75 | 3 | 1.5 | 0.75 | 6.2 | 1.5 |
| Calcium Chloride (anhydrous) | 113.2 | — | 28.31 | 113.24 | 56.62 | 72.5 | 113.24 | 72.5 |
| Calcium Chloride 2H$_2$O | — | 0 | 50 | — | — | — | — | — |
| Calcium Nitrate 4H$_2$O | — | 208.4 | — | — | — | 386 | — | 386 |
| Cobalt Chloride 6H$_2$O | 0.03 | — | 0.006 | 0.025 | 0.0125 | — | 0.025 | — |
| Cupric Sulfate 5H$_2$O | 0.03 | 0.01 | 0.006 | 0.025 | 0.0125 | 0.25 | 0.025 | 0.25 |
| Na$_2$ EDTA 2H$_2$O | 37.3 | — | 9.32 | 37.3 | 18.65 | 37.3 | 37.3 | 37.3 |
| Ferric Sulfate | — | 2.5 | — | — | — | — | — | — |
| Ferrous Sulfate 7H$_2$0 | 27.8 | — | 6.95 | 27.8 | 13.9 | 27.8 | 27.8 | 27.8 |
| Magnesium Sulfate (anhydrate) | 122.1 | 366.2 | 30.5 | 122.09 | 61.04 | 180.7 | 122.09 | 180.7 |
| Manganese Sulfate H$_2$O | 10 | 23.788 | 22.5 | 10 | 5 | 22.3 | 10 | 22.3 |
| Molybdenum Trioxide | — | 0.001 | — | — | — | — | — | — |
| Molybdic Acid (sodium salt) 2H$_2$O | 0.25 | — | 0.062 | 0.25 | 0.125 | 0.25 | 0.25 | 0.25 |
| Potassium Chloride | — | 65 | — | — | — | — | — | — |
| Potassium Iodide | 0.75 | 0.75 | 0.175 | 0.75 | 0.375 | — | 0.75 | — |
| Potassium Nitrate | 2500 | 80 | 625 | 2500 | 1250 | — | 2500 | — |
| Potassium Phosphate (monobasic) | — | — | 10 | — | — | 170 | — | 170 |
| Potassium Sulfate | — | — | — | — | — | 990 | — | 990 |
| Sodium Phosphate (monobasic anhydrous) | 130.5 | 16.5 | 32.62 | 130.5 | 65.25 | — | 130.5 | — |
| Sodium Sulfate | — | 200 | — | — | — | — | — | — |
| Zinc Sulfate 7H$_2$O | 2 | 3 | 0.5 | 2 | 1 | 8.6 | 2 | 8.6 |
| Myo-Inositol | 100 | 100 | 125 | 100 | 50 | 100 | 100 | 100 |
| Nicotinic Acid | 1 | — | 0.75 | 1 | 0.5 | 1 | 1 | 1 |
| Pyridoxine-HCl | 1 | — | 0.25 | 1 | 0.5 | 1 | 1 | 1 |
| Thiamine-HCl | 10 | 5 | 3.5 | 10 | 5 | 10 | 10 | 10 |
| Glutamine | 292.6 | 146.4 | — | 292.8 | 292.8 | 1756.8 | — | 292.8 |
| Tryptophan | — | — | — | — | — | — | — | — |
| Phenylalanine | — | 30 | — | — | — | — | — | — |
| Lysine | — | 20 | — | — | — | — | — | — |
| Methionine | — | — | — | — | — | — | — | — |
| Sodium Acetate | — | 10 | 10 | — | — | — | — | — |
| Sucrose | 10000 | 50000 | 40000 | 10000 | 10000 | 10000 | 20000 | 10000 |
| N$_6$-Benzyladenine | 0 | 2 | 2 | 0.002 | 0.002 | — | — | — |
| Ascorbic Acid | 50 | 100 | 50 | 100 | 100 | 100 | 100 | 100 |
| Picloram | — | — | — | 1.2 | 2.4 | 1.2 | — | 1.2 |

TABLE 4-continued

Chemical Composition of Various Growth Medium

| Chemical Ingredient | A | B | C | D | E | F | G | H |
|---|---|---|---|---|---|---|---|---|
| Casein Hydrolysate | — | — | 500 | — | — | — | 1000 | — |
| 6-Dimethyltallylamino Purine | — | — | — | — | — | 0.02 | — | — |
| Kinetin | — | — | — | — | — | — | — | 0.02 |
| pH | 5.6 | 5.6 | 5.6 | 5.6 | 5.6 | 5.6 | 5.6 | 5.6 |
| β-Naphthaleneacetic Acid | 0.931 | 10 | — | — | — | — | 1.862 | — |

Example 2

Suspension Initiation and Growth of Suspended Cells

One gram of callus material was aseptically inoculated into a 125 ml Erlenmeyer flask containing 25 ml of liquid medium (Table 4). The flask was covered with a silicone foam cap and placed on a gyratory shaker at 120 rpm at 24° C. in darkness. Suspension cultures were formed in approximately 3–10 days. Medium exchanged was initiated by suction filtering the flask contents through a buchner funnel containing a miracloth filter and resuspending all the biomass in fresh medium. One to two grams of cells were transferred into a 125 ml flask containing 25 ml of fresh medium weekly. Typical growth rates and cell densities achieved in suspension cultures of representative species are listed in Table 5.

TABLE 5

Growth Profile of *Taxus Cells*

| Species | Dry Weight Doubling Time | Fresh Weight Doubling Time | Dry Wt. Density | Fresh Wt. Density |
|---|---|---|---|---|
| T. brevifolia | 2.0 days | 3.5 days | 20 g/L | 400 g/L |
| T. baccata | 2.0 days | 6.0 days | 15 g/L | 220 g/L |
| T. chinensis | 2.5 days | 4.5 days | 20 g/L | 285 g/L |
| T. canadensis | | 8.5 days | 13 g/L | 260 g/L |

Figure 4:
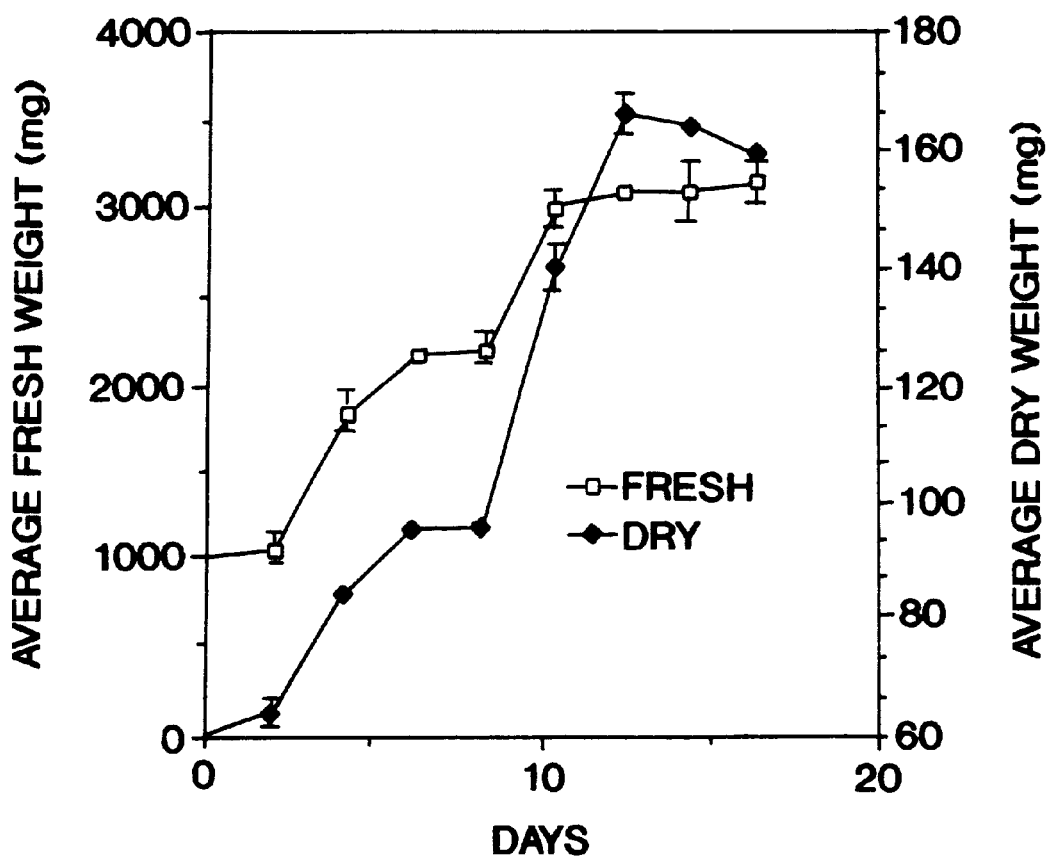
FIG. 4 Biomass increase in a *Taxus chinensis* suspension culture line K-1.

The increase in biomass (fresh and dry weight) with time for *T. chinensis* line K-1 was plotted in FIG. 4. The maximal growth rate was determined by measuring the slope at points of most rapid biomass increase. Cell cultures of *T. chinensis* with a maximum doubling time of 2.5 days, has a growth rate significantly higher than previously reported for Taxus species suspension cultures. Typical Taxus cultures have doubling times of about 7–12 days.

Culturing cells at high density maximizes the productivity of the cell culture process. Whereas previous cultures of *T. brevifolia* has a cell density of less than 1 gram dry weight per liter (Christian et al., 1991), suspension cultures *T. chinensis* can reach densities up to 8–20 grams dry weight per liter after 18 days of growth. Cell viability was determined by staining with a 0.05% fluorescein diacetate (FDA) in acetone (J. M. Widholm, Stain Technol 47:189–94, 1972) followed by counting the number of green fluorescein cells upon excitation with blue light in a fluorescence microscope. Cell viability was higher than 90% throughout the growth phase.

Example 3

Viability of Taxus Cells After Preculturing with Mannitol

Six to 7 day old suspension cultures of Taxus cells were harvested and resuspended into fresh growth medium containing 0.16M mannitol, 0.22M mannitol, 0.33M mannitol or 0.44M mannitol.

After 3 days of incubation in growth medium with mannitol, cells were cold acclimated at 4° C. for 3 hours. Acclimated cells were harvested and transferred to 4 ml cryovials containing a cold vitrifying solution of 40/30 wt % ethylene glycol/sorbitol in media. The vials were incubated at 4° C. for 3 minutes and frozen by immersion into liquid nitrogen. Vials were maintained in liquid nitrogen for at least 10 minutes before use in the thawing experiments.

Vials of frozen cells were removed from liquid nitrogen storage and agitated at 40° C. until the contents are liquefied (1–2 minutes). The liquefied cells were then washed 5 to 6 times with sterile media containing 1 M sorbitol, 3 times with media containing 0.5 M sorbitol media, 3 times with 0.1 M sorbitol media, and 3 times with sorbitol free media. Washing was performed by resuspension of cells in wash media, centrifugation at 50× g for 2 minutes and aspiration of wash media from the cell pellet. Cell viability was determined immediately after thawing. The summary of multiple experiments is listed below.

TABLE 6

Post Thaw Viability of Cells Pretreated with Mannitol

| Concentration | Viability | Regrowth |
|---|---|---|
| 0.16M | 60% | vigorous |
| 0.22M | 30% | slight |
| 0.33M | 30% | slight |
| 0.44M | 20% | slight |

Example 4

Viability of Taxus Cells After Preculturing With Sorbitol

Frozen Taxus cells were thawed and suspended into fresh growth medium containing sorbitol at 0.15 M, 0.22 M, 0.33 M, 0.44 M and 0.80 M sorbitol. Cell viability was determined immediately after thawing. A summary of the results from multiple trials are listed below:

TABLE 7

Post Thaw Viability of Cells Pretreated with Sorbitol

| Concentration | Viability | Regrowth |
|---|---|---|
| 0.15M | 20% | none |
| 0.22M | 40% | vigorous |

TABLE 7-continued

Post Thaw Viability of Cells Pretreated with Sorbitol

| Concentration | Viability | Regrowth |
|---|---|---|
| 0.33M | 30% | vigorous |
| 0.44M | 20% | vigorous |
| 0.80M | 20% | slight |

Example 5

Viability of Taxus After Preculturing With Sucrose

Six to seven day old cell suspensions in growth medium were harvested and the cell biomass resuspended in fresh growth medium containing 0.06 M, 0.12 M, 0.15 M, 0.29 M and 0.58 M sucrose. Cells were cryopreserved, frozen, thawed and osmotically adjusted accordingly. Cell viability was determined immediately after thawing. A summary of the results from multiple experiments are listed in Table 8:

TABLE 8

Post Thaw Viability of Cells Pretreated with Sucrose

| Concentration | Viability | Regrowth |
|---|---|---|
| 0.06M | 40% | slight |
| 0.12M | 40% | slight |
| 0.15M | 40% | slight |
| 0.29M | 30% | slight |
| 0.58M | <15% | slight |

Example 6

Effects of Osmotic Agents on the Survival of Taxus Cells

Various osmotic agents in growth medium were evaluated to determine their effects on the survival of Taxus species cells precultured with the agents, after the preculture period and after thawing of the cryoprotected and frozen Taxus cell suspensions. Cells of three-day cell culture suspensions were precultured in growth medium containing various osmotic agents prior to cryoprotection. Cryoprotected cells were frozen and stored in liquid nitrogen for a minimum of one hour. Viability tests were performed at the end of the preculture period (control) and immediately after thawing of the cryoprotected and frozen cell.

Cell cultures pretreated with mannitol in growth medium exhibited the highest percent viability upon thawing after cryoprotection and freezing as compared to viability observed using the other osmotic agents.

TABLE 9

Effects of Osmotic Agent on Post Thaw Viability

| | Concentration Survival (Viability) | |
|---|---|---|
| Osmotic Agent | Control | Frozen |
| Proline | <50% | <15% |
| Trehalose | 50–95% | <15% |
| Sucrose | 50–95% | 20–50% |
| Sorbitol | 50–95% | 30–70% |
| Mannitol | 50–95% | 40–80% |

Example 7

Effect Osmotic Agents and Cryoprotectants on Taxus Viability

Cells of Taxus suspension cultures (KS1A) were harvested and precultured with various osmotic agents in the medium. Osmotic agents tested include trehalose, proline, sorbitol (0.15 M–0.8 M), sucrose (2–20%) and mannitol (0.16 M). Viability was evaluated for each cell suspension at the end of the preculture period and immediately after thawing. Regrowth was evaluated after post-thaw osmotic adjustment. The vitrification solutions used were ethylene glycol/sorbitol/pectin and ethylene glycol/sorbitol at 40/30 weight percent in culture medium. The results are summarized in Table 10. The highest percent viability and most rigorous regrowth were observed when mannitol was used for preculturing and ethylene glycol/sorbitol was used as the cryoprotectants in the vitrification solution.

TABLE 10

Effects of Osmotic Agents and Cryoprotectants of Post Thaw Viability

| Osmotic Agent | Viability | Cryoprotectants | Post-Thaw Recovery Viability | Growth |
|---|---|---|---|---|
| Trehalose and Proline | 50–95% | Ethylene glycol/Sorbitol/pectin | <15% | none |
| Sorbitol 0.15M–0.8M | 50–95% | Ethylene glycol/Sorbitol | 30–70% | slight to vigorous |
| Sucrose 2%–10% | 50–95% | Ethylene glycol/Sorbitol | <10–40% | none to vigorous |
| Mannitol | 75–95% | Ethylene glycol/Sorbitol | 40–80% | slight to vigorous |

Example 8

The Effect of Preculture Length on Survival

Taxus cells were harvested from cell culture and the biomass resuspended in growth medium containing mannitol at a concentration of 3% for one day or three-days at room temperature. Loaded cells were incubated at 4° C. for 3 hours and transferred to 4 ml cryovials containing cold vitrifying solution which comprising 40/30 weight percent ethylene glycol/sorbitol in culture medium. The vials were incubated at 4° C. for three minutes and frozen by liquid nitrogen immersion. Cells contained in the vials were maintained in liquid nitrogen for at least 10 minutes.

Cryopreserved cells were thawed and their viability was determined by FDA and trypan blue staining procedures. Cells precultured with mannitol for three days exhibited significantly higher post-thaw availability than cells which were not precultured in medium containing mannitol.

TABLE 11

Effects of Preculture Time on Viability

| Days of Preculture | Survival Control | 3% Mannitol |
|---|---|---|
| 1 | 5–10% | 50% |
| 3 | 5–15% | 40–80% |

Example 9

Effect of Ethylene Glycol/Sorbitol on Thawed Taxus Cell Viability

Six to seven day cell suspensions of Taxus species cell line KS1A were pretreated with 3% mannitol for three days at room temperature. Loaded cells were acclimated to the cold by incubating the flasks at 4° C. for 3 hours. Cold acclimated cells were transferred to 4 ml cryovials and cold vitrification solution was added to each and mixed. After vitrification at 4° C. for three minutes, cells were frozen by liquid nitrogen immersion. Vials were maintained in liquid nitrogen for at lease 10 minutes.

Cryopreserved cells were thawed by transferring vials from liquid nitrogen and agitated in a 40° C. water bath for 1–2 minutes. Post-thaw viability was determined by FDA staining assay.

Ten trials evaluating cell suspensions of Taxus species cell line KS1A were performed with different concentrations of ethylene glycol/sorbitol. The results are summarized in Table 12. Cell suspensions frozen in the vitrification solution containing ethylene glycol/sorbitol at a concentration of 40/30 wt %, exhibited the highest post-thaw percent viability as well as the most vigorous regrowth as compared to cells vitrified using other concentrations of ethylene glycol/sorbitol.

TABLE 12

Effects of Vitrification Solution of Recovery

| Ethylene Glycol/Sorbitol | Post-Thaw Viability | Regrowth |
| --- | --- | --- |
| 50%/30% | 20% | slight |
| 45%/35% | 25% | slight |
| 40%/40% | 25% | slight |
| 40%/30% | 60% | vigorous |
| 38%/32% | 40% | vigorous |
| 36%/34% | 35% | moderate |
| 35%/35% | 35% | moderate |
| 30%/40% | 40% | slight |
| 30%/40% | 40% | slight |
| 20%/50% | 25% | none |

Example 10

Effects of Cryoprotectants of Taxus Cells Survival After −196° C. Storage

Cultured Taxus cells were harvested and resuspended in fresh growth medium containing 3% mannitol for 3 days. Cells were cold acclimated for 3 hours and transferred to cryovials containing vitrification solution. Cell suspensions were frozen by liquid nitrogen immersion. Liquid nitrogen frozen cells were thawed by agitating the cryovials in a 40° C. water bath for 1–2 minutes. Cells frozen with ethylene glycol as a cryoprotectant has the highest viability.

TABLE 13

Effects of Cryoprotectants on Viability

| Cryoprotectant | Concentration | Viability |
| --- | --- | --- |
| DMSO | 5%–30% | ≦15% |
| Propylene Glycol | 15 % | 0 |
| Glycerol | 20%–30% | 0 |
| PEG-8000 | 10% | 0 |
| Ethylene Glycol | 20%–50% | 25%–80% |

Example 11

Viability of Taxus Cells as a Function of Biomass to Vitrifying Solution

Six to seven day old cell suspension of taxus species cell line KS1A were harvested and resuspended in fresh medium containing 3% mannitol and incubated for three days at room temperature. Following cold acclimation at 4° C. for 3 hours, cells were transferred to 4 ml cryovials containing 40/30 wt % ethylene glycol/sorbitol in culture medium. Vials were incubated at 4° C. for 3 minutes and frozen by liquid nitrogen immersion. Vials were maintained in liquid nitrogen for at least 10 minutes before thawing.

The highest percent viability was observed when the cell biomass/vitrifying solution quantity was 167 mg/ml. Acceptable viability was also when the cell biomass/vitrifying solution ratio was 143, 200 and 250 mg/ml.

TABLE 14

Effects of Cell Biomass on Viability

| Cell Biomass/Vitrifying Solution | Viability |
| --- | --- |
| 143 mg/ml | 60% |
| 167 mg/ml | 80% |
| 200 mg/ml | 45% |
| 250 mg/ml | 45% |
| 300 mg/ml | ≦10% |
| 400 mg/ml | ≦10% |
| 500 mg/ml | ≦5% |
| 1,000 mg/ml | ≦5% |

Example 12

Effects of Different Method Steps on Taxus Cell Viability

Different method steps were evaluated to determine the steps which would result in the highest percent post-thaw viability. Cells were cryopreserved with and without cryoprotectants, with and without osmotic pretreatments, with and without cold treatment, and with and without vitrification.

In the first trial, six to seven day old Taxus cells cultures were frozen with and without cryoprotectants. In the second trial, cells were frozen with and without a 40/30, weight percent, ethylene glycol/sorbitol vitrification solution treatment. In the third trial, cells were vitrified and frozen with and without a pretreatment comprising a three day incubation in 3% mannitol growth media. In the fourth trial, cells were pretreated and vitrified and frozen with or without cold acclimation.

For each trial, viability tests were performed immediately after thawing. Cells precultured with growth medium containing 3% mannitol for 3 days at room temperature, followed by a 2–4 hour cold treatment prior to cryoprotection, exhibited the highest percent viability. Suitable viability was also observed in cells precultured for 3 days in medium containing 3% mannitol and subjected to cryoprotection without previous cold treatment, and in cells preculture in growth medium for 3 days and precultured in media containing mannitol for 24 hours followed by a 2 to 4 hour cold treatment prior to cryoprotection.

TABLE 15

Viability of Cells Recovered from Liquid Nitrogen

| Treatment | Viability | Regrowth |
| --- | --- | --- |
| Cells in medium Direct plunging into liquid nitrogen | 0 | none |

TABLE 15-continued

Viability of Cells Recovered from Liquid Nitrogen

| Treatment | Viability | Regrowth |
|---|---|---|
| Cells in medium cryoprotection liquid nitrogen | ≦10 | none |
| Cells in medium precultured 3 days in 3% mannitol cryoprotection liquid nitrogen | 40–60 | slight |
| Cells in medium Precultured 3 days in 3% mannitol 2–4 hour cold treatment cryoprotection liquid nitrogen | 40–80 | vigorous |
| Cells in growth medium for 3 days preculture in osmotic media for 24 hours 3% mannitol 2–4 hour cold treatment cryoprotection liquid nitrogen | 40–60 | vigorous |

Cells were again tested for viability tests using the indicated steps, performed according to the methods described herein.

TABLE 16

Viability of Cells Recovered from Liquid Nitrogen

| Treatment | Viability | Regrowth |
|---|---|---|
| Freeze Dried Liquid nitrogen | 20% | none |
| Freeze Dried Vitrification Liquid nitrogen | 30–60% | moderate |
| Freeze Dried Preculture in sorbitol Liquid nitrogen | 20–40% | slight |
| Freeze Dried Preculture in sorbitol Vitrification Liquid nitrogen | 30–60% | moderate |
| Freeze Dried Loading Vitrification Liquid nitrogen | 20–40% | slight |
| Freeze Dried Loading Vitrification Liquid nitrogen | 30–50% | good |
| Preculture in sorbitol Freeze Dried Vitrification Liquid nitrogen | 40–60% | good |
| Preculture in mannitol Freeze Dried Vitrification Liquid nitrogen | 40–60% | good |
| Preculture in sucrose Freeze Dried Vitrification Liquid nitrogen | 40–60 % | good |

Example 13

Cell Viability and Growth Before and After Cryopreservation

The following Taxus species cell lines were evaluated to determine cell viability and regrowth after cryopreservation: KS1A; KEIR; 647; 1224; 12–6;12–14; and 12–20.

Six to seven day old cell suspensions of each cell line were harvested and the biomass resuspended in fresh growth medium containing 3% mannitol. Cells were incubated for 3 days at room temperature and thereafter the loaded cells suspensions were incubated at 4° C. for from 3 hours. Cold acclimated cells were transferred to 4 ml cryovials containing a cold vitrification solution of ethylene glycol/sorbitol 40/30 wt %. The vitrification solution and cells were gently mixed and the vials were incubated at 40° C. for 3 minutes. Thereafter, the cell suspensions were frozen by liquid nitrogen immersion for at least 10 minutes.

After freezing, the cells were thawed by transferring the frozen vials from liquid nitrogen to a 40° C. water bath for 1–2 minutes. Post-thaw cell viability was determined by FDA staining assay. Cells were washed 5–6 times with cold sterile 1M sorbitol media and resuspended in fresh 1 M in medium.

The cell suspensions free from toxic cryoprotectants were then each separately filtered using a buchner funnel and Whatmann 541 filter paper under sterile conditions. For each cell suspension, the filter with cells was layered on semisolid growth medium containing 0.5M sorbitol and equilibrated for 30 minutes at room temperature. Paper containing cells was transferred to solid growth medium containing 0.1M sorbitol and incubated for 24 hours. The paper with cells was transferred to semisolid growth medium without sorbitol and incubated for 24 hours at room temperature. The filter containing cells was then again transferred to fresh semisolid growth medium without sorbitol and incubated at room temperature for an additional 24 hours. Callus cell growth on the semisolid nutrient media was evident at about 2 to 3 weeks. Thereafter, cell suspensions in liquid growth medium were initiated from the callus.

As can be seen from Table 17 set forth below, all of the cell lines evaluated exhibited acceptable post-thaw viability and recovery growth.

TABLE 17

Effects of Preculture Conditions on Viability

| Cell Line | Preculture Condition | Viability | Cryo-Protectants | Post-Thaw Viability | Recovery Growth |
|---|---|---|---|---|---|
| KS1A | 3% mannitol 3 days | ≧95% | ethylene glycol/ sorbitol 40/30 wt % | 40–80% | vigorous |
| KEIR | 3% mannitol 3 days | ≧95% | ethylene glycol/ sorbitol 40/30 wt % | 30–60% | slight |
| 647 | 3% mannitol 3 days | ≧95% | ethylene glycol/ sorbitol 40/30 wt % | 30–60% | slight |
| 1224 | 3% mannitol 3 days | ≧95% | ethylene glycol/ sorbitol 40/30 wt % | 40–60% | vigorous |

TABLE 17-continued

Effects of Preculture Conditions on Viability

| Cell Line | Preculture Condition | Viability | Cryo-Protectants | Post-Thaw Viability | Recovery Growth |
|---|---|---|---|---|---|
| 12-6 | 3% mannitol 3 days | ≥95% | ethylene glycol/ sorbitol 40/30 wt % | 40% | vigorous |
| 12-14 | 3% mannitol 3 days | ≥95% | ethylene glycol/ sorbitol 40/30 wt % | 30% | vigorous |
| 1220 | 3% mannitol 3 days | ≥95% | ethylene glycol/ sorbitol 40/30 wt % | 35% | vigorous |

Example 14

Growth and Product Formation of Taxus Cells Upon Cryopreservation

Six to seven day cell suspensions of Taxus cell line KS1A were cryopreserved and thawed. The cells were precultured with 3% mannitol in growth medium for 3 days and 40/30 wt % ethylene glycol/sorbitol was used as a cryoprotectants. Growth doubling time and product formation were evaluated before and after freezing and thawing. Product yield was monitored after 5 days of growth in suspension. Nuclear DNA content in the cells was monitored by flow cytometry and found to be about 22.7 pg/nuclei before and 22.9 pg/nuclei after cryopreservation. Cryopreservation did not affect product production.

TABLE 18

Growth and Product Formation of *Taxus* before and after $LN_2$

| Preculture Treatments | Cryo-Protectant | (Doubling Time) | Product Formation (mg/L) | | |
|---|---|---|---|---|---|
| | | | Taxol | Baccatin | 10-DAB |
| 3% mannitol | ethylene glycol/ sorbitol/ (40/30 wt %) | 7 (5–7) | 0.2 | 1.1 | 0.4 |
| | — | 7 (5–7) | 0.2 | 1.1 | 0.4 |

Example 15

Growth and Product Formation in Taxus Cells After Cryopreservation

Taxus species cell lines were cryopreserved and subsequently thawed and subjected to post-thaw osmotic adjustment. Growth and product formation were determined after the establishment of cell suspensions in liquid culture. Growth reflects the average doubling time of cell suspensions in days after they were established in growth medium. Product formation was determined after 14 days of growth in suspension. Results are listed in Table 19.

TABLE 19

Taxol Production of Cells Recovered from Cryopreservation

| Cell Line | (Average doubling time in days) | Production (mg/L - 14 days) | | |
|---|---|---|---|---|
| | | Taxol | Baccatin | 10-DAB |
| Keir | 4 | 10.5 | 10.6 | 3.4 |
| KS1A | 5.5 | 22.6 | 7.4 | 2.3 |
| 1224 | 5.5 | 10.8 | 73 | 13 |
| SS3-184 | 7 | — | — | — |
| SS12-6 | 5.8 | 25 | 51 | 6.7 |
| SS12-19 | 6 | 9.2 | 31 | 4.7 |
| SS12-20 | 5.5 | 10 | 24 | 4.4 |
| SS12-79 | 5 | 2.4 | 9.6 | 1.9 |
| SS12-99 | 8.5 | — | — | — |
| SS12-103 | 6 | 19.3 | 68.5 | 14.3 |
| 647 | 5.5 | — | — | — |

Figure 5A:
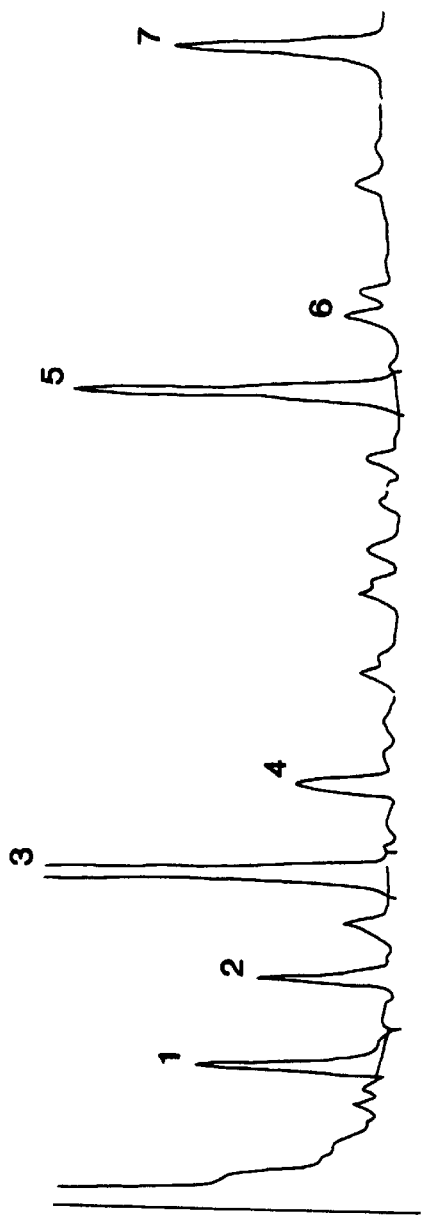
FIG. 5 Chromatograms of (A) cells cryopreserved for 6 months in comparison with (B) non-cryopreserved cells.
Figure 5B:
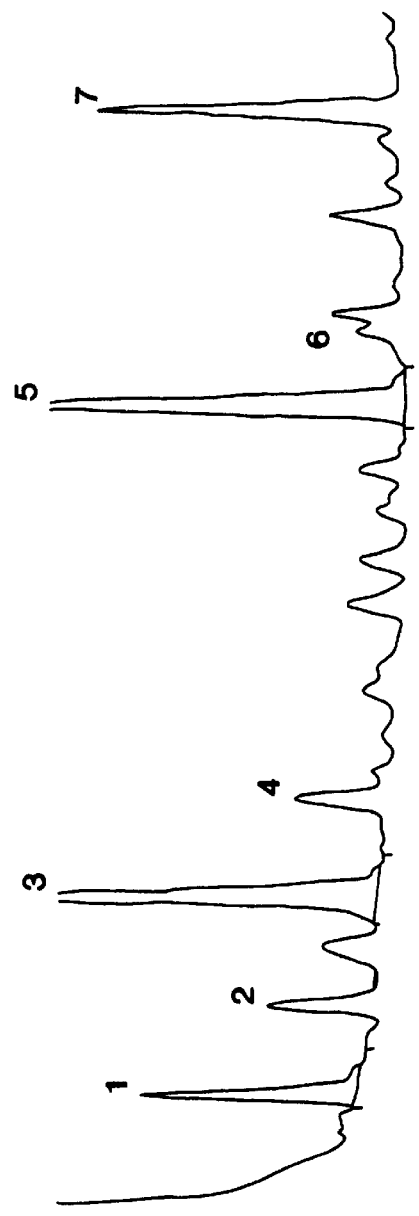

FIG. 5 illustrate chromatograms of the extracellular fraction at day 20 from Taxus species cell line 1224 where (A) represents the control cell suspension Which was not cryopreserved and (B) represents the cell suspension regenerated after cryopreservation, freezing, storage for six months, and thawing and post-thaw osmotic adjustment. Peak 1 is 10-deacetylbaccatin; peak 2 is 9-dihydrobaccation III; peak 3 is baccatin III; peak 4 is 9-dihydro-13-acetylbaccatin III; peak 5 is taxol; peak 6 is 2-benzoyl-2-deacetylbaccatin and peak 7 is 2-benzoyl-2-deacetyl-1-hydrozybaccatin I.

FIG. 6 illustrate chromatograms of the extracellular fraction at day 20 from Taxus species cell line 203 where (A) represents the control cell suspension Which was not cryopreserved and (B) represents the cell suspension regenerated after cryopreservation, freezing, storage for three months, and thawing and post-thaw osmotic adjustment. Peak 1 is 10-deacetylbaccatin; peak 2 is 9-dihydrobaccation III; peak 3 is baccatin III; peak 4 is 9-dihydro-13-acetylbaccatin m; peak 5 is taxol and peak 6 is 2-benzoyl-2-deacetylbaccatin. As can be seen from FIGS. 5 and 6, the product formation profile is substantially the same in the control cell suspension and the regenerated cell suspension.

Example 16

Genetic Stability of Cryopreserved and Non-Cryopreserved Cells

Figure 7:
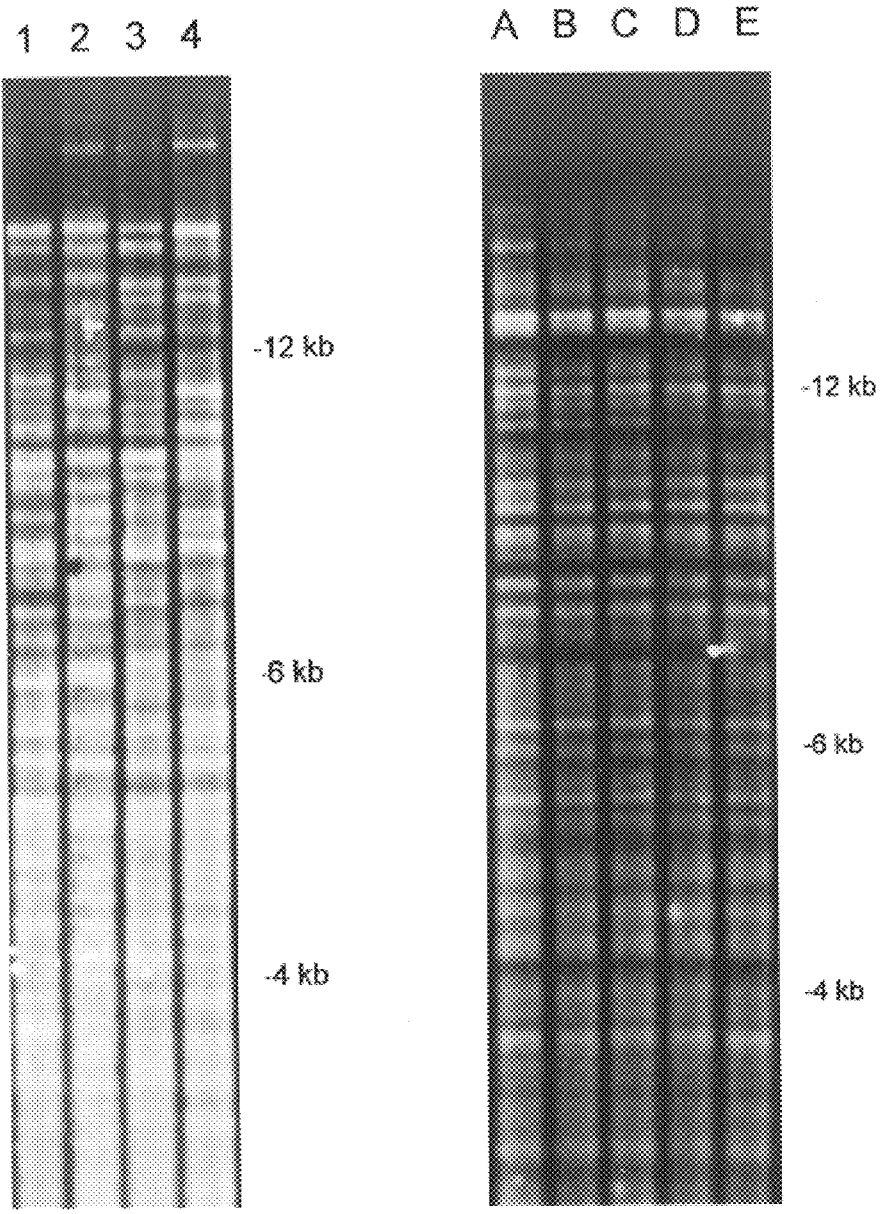
FIG. 7 Southern blot analysis of the genetic stability of cryopreserved cells.

Cell lines were established from a single *Taxus chinensis* var. *mairer* tree. One of these established cell lines was cultured, cryopreserved for one year, and thawed. Genetic analysis was performed on cells from the original tree and on the cryopreserved cells to determine if cryopreservation have affected genetic stability of the cells. Briefly 10 μg of total DNA from each cell line was and treated with a four fold over digestion of restriction endonuclease and size fractionated by agarose gel electrophoresis. The size fractionated DNA was transferred to a nitrocellulose solid support and hybridized to a radio labeled nucleic acid probe, Jeffrey's 33.6 minisatellite probe. This hypervariable region probe shows different banding patterns from the DNA of 4 separate trees in lanes 1–4 of FIG. 7. In contrast, the initial isolate (lane A), cells cultured for 1 year (lane B), and cells cryopreserved for 1 year (lane C) was identical genetically from cells isolated from the same tree one year later (lanes D and E). Cryopreservation did not result in any mutation detectable by this analysis.

Example 17

Stability of Cryopreserved Taxus Cells

Figure 8:
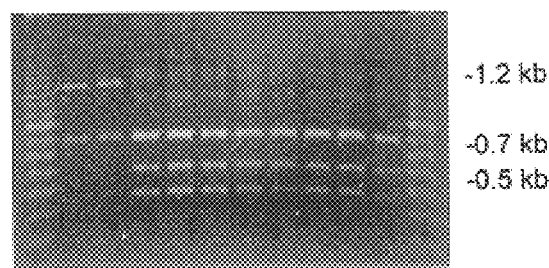
FIG. 8 PCR analysis of the genetic stability of cryopreserved cells.

To determine if the length of cryopreservation has any effect on genetic stability, Taxus cell lines 1224 was frozen for one hour to 6 months and analyzed for their genetic stability. DNA was extracted from viable cultures grown thawed and re-established from these cryopreserved cells. A 3.1 Kb polymorphic region of the genome containing nuclear ribosomal coding and non-coding DNA was amplified by polymerase chain reaction and digested with endonuclease DpnII. The digested DNA was sorted by size using gel electrophoresis and visualize after ethidium bromide staining. The results of the analysis is shown in FIG. 8. The original cell line and a noncryopreserved cell line were analyzed in lanes C and D respectively. Two unrelated cell lines established from unrelated trees show a different digestion pattern. In contrast, no genetic mutation was detected in cells cryopreserved for one hour (lane E), one day (lane F), one week (lane G), one month (lane H) or 6 months (lane I and J). The banding pattern of these cryopreserved and non-cryopreserved cells were all identical (lanes C to J).

Example 18

Cryopreservation of Tomato Cell Lines

For successful cryopreservation of tomato cell lines, loading and vitrification solutions were added gradually in a stepwise fashion to reduce osmotic shock. Loading and vitrification solutions comprised of 30% (w/v) glycerol, 15% (w/v) ethylene glycol and 15% (w/v) dimethylsulfoxide. Without gradual addition, cells did not grow rapidly after the post-thawing recovery period. The effect of post-thaw viability and recovery regrowth was examined and the results are shown in Table 20.

TABLE 20

Effects of Preculturing Conditions on Viability and Recovery Regrowth of a Tomato Cell Line

| Osmotic Agent - Conc. | Preculturing Duration (Percent Viability) | | | |
|---|---|---|---|---|
| | 1 Day | 2 Days | 3 Days | 6 Days |
| Sucrose - 0.06 M | 5 (−) | 10 (−) | 15 (+) | 15 (+) |
| 0.1 M | 20 (+) | 30 (++) | 35 (++) | 40 (++) |
| 0.3 M | 35 (++) | 35 (++) | 50 (+++) | 60 (+++) |
| 0.5 M | 45 (+++) | 60 (+++) | 65 (+++) | 30 (++) |
| 0.8 M | 50 (+++) | 30 (+++) | 10 (−) | 10 (−) |
| Sorbitol - 0.06 M | 10 (−) | 15 (+) | 20 (+) | 30 (+) |
| 0.1 M | 15 (+) | 20 (++) | 40 (++) | 60 (+++) |
| 0.3 M | 30 (++) | 40 (++) | 70 (+++) | 50 (+++) |
| 0.5 M | 20 (+) | 40 (++) | 35 (++) | 10 (+) |
| 0.8 M | 10 (−) | 30 (+++) | 20 (+) | 5 (−) |
| Mannitol - 0.06 M | 5 (−) | 5 (−) | 10 (−) | 10 (−) |
| 0.1 M | 15 (+) | 30 (++) | 35 (++) | 40 (++) |
| 0.3 M | 40 (++) | 45 (++) | 50 (+++) | 20 (+) |
| 0.5 M | 30 (++) | 40 (++) | 35 (++) | 15 (+) |
| 0.8 M | 20 (+) | 35 (++) | 15 (+) | 5 (−) |

(−) = no recovery regrowth of callus
(+) = slight recovery regrowth of callus
(++) = moderate recovery regrowth of callus
(+++) = vigorous recovery regrowth of callus The highest viability (survival of cells) was obtained when cells were precultured for three days in liquid nutrient media containing 0.5 M sucrose or 0.3 M sorbitol, 65% and 70% respectively. These preculturing conditions also supported vigorous growth of cells upon post-thawing of cell suspensions. Successful cryopreservation also depended on the preculture period and the concentration of the osmotic agent. Prolonging the preculture period to ten days and increasing the concentrations of osmotic agents to greater than 0.8M did not increase viability of the cells. Without preculture, cells did not survive $LN_2$ temperatures either with one step or with stepwise loading and vitrification solution addition methods.

Viability and regrowth recovery was further enhanced by exposing precultured cells to a heat-shock treatment up to four hours, and by the addition of divalent cations ($CaCl_2$, $MgCl_2$). This approach has also been successfully used in the cryopreservation of cell lines derived from species of Lupinus, Sophora, Conospernum, Nicotiana and Solanum as well as the recalcitrant cell lines derived from various Taxus species such as *Taxus chinensis*. In many instances, regrowth of cell lines of these plant species was macroscopically visible 3 to 4 days after plating as compared to 6 to 10 days with one step loading and vitrification methods. Post-thaw wash of cell biomass with liquid medium containing ethylene action inhibitors or ethylene biosynthesis inhibitors further improved the quality of recovered cell lines. Viability rates of 90% were consistently achieved and faster growth rates were observed after cell suspensions were established from these lines.

Other embodiments and uses of the invention will be apparent to those skilled in the art from consideration of the specification and practice of the invention disclosed herein. All U.S. patents cited herein are hereby specifically incorporated by reference in their entirety. The specification and examples should be considered exemplary only with the true scope and spirit of the invention indicated by the following claims.

I claim:

1. A method for cryopreserving a plant cell comprising the steps of: preculturing the plant cell with a divalent cation at greater than about 5 mM and an osmotic agent for a period of time effective to stabilize cell membranes; and in any order, loading the plant cell with a cryoprotecting agent; and vitrifying the plant cell with a cryoprotection solution; and freezing the plant cell at a cryopreservation temperature.

2. The plant cell of claim 1 which is a species of Taxus, Solanum, Legume, Lycopersicum, Abies, Cypressus, Ginkgo, Juniperus, Picea, Pinus, Pseudotsuga, Sequoia, Tsuga, Zamia, Avena, Cocos, Dioscorea, Hordeum, Musa, Oryza, Saccharum, Sorghum, Triticum, Zea, Achyrocline, Atropa, Brassica, Berberis, Capsicum, Catharanthus, Conospermum, Datura, Daucus, Digitalis, Echinacea, Eschscholtzia, Glycine, Gossypium, Hyoscyamus, Malus, Medicago, Panax, Pisum, Rauvolfia, Ruta, Trichosanthes or Nicotiana.

3. The plant cell of claim 2 wherein the Taxus species is *T. baccata, T. brevifolia, T. canadensis, T. chinensis, T. cuspidata, T. floridana, T. globosa, T. media, T. nucifera* or *T. wallichiana*.

4. The method of claim 1 wherein the plant cell is obtained from new growth needles, bark, leaves, stem, root, rhizome, callus cells, protoplasts, cell suspensions, meristems, seeds or embryos.

5. The method of claim 1 wherein preculturing involves culturing said plant cell in medium containing the osmotic agent and the divalent cation for between about 1 day and about 6 days.

6. The method of claim 1 wherein the osmotic agent is sucrose, sorbitol or mannitol at a concentration of between about 0.06 M and about 0.8 M.

7. The method of claim 1 wherein the divalent cation is $CaCl_2$, $MgCl_2$ or $MnCl_2$.

8. The method of claim 1 wherein the divalent cation is at a concentration of from about 5 mM to about 20 mM.

9. The method of claim 1 wherein loading comprises incubating said plant cell in the cryoprotection solution comprising between about 0.5% to about 30%, by weight, of the cryoprotecting agent.

10. The method of claim 9 wherein the cryoprotecting agent is selected from the group consisting of DMSO, propylene glycol, glycerol, polyethylene glycol, ethylene glycol, butanediol, formamide, propanediol, sorbitol, mannitol and mixtures thereof.

11. The method of claim 1 wherein the cryoprotecting agent is selected from the group consisting of DMSO, propylene glycol, glycerol, polyethylene glycol, ethylene glycol, butanediol, formamide, propanediol, sorbitol, mannitol and mixtures thereof.

12. The method of claim 1 wherein the osmotic agent and the cryoprotecting agent are the same.

13. The method of claim 1 wherein loading and vitrifying are conducted simultaneously.

14. The method of claim 1 wherein loading or vitrifying is performed in a single step or in a plurality of steps.

15. The method of claim 14 wherein the plurality of steps comprises adding the cryoprotecting agent to the plant cell five times at one minute intervals.

16. The method of claim 1 wherein the cryopreservative temperature is less than about −70° C.

17. The method of claim 1 further comprising the step of including a stabilizer during preculturing, loading or vitrifying.

18. The method of claim 17 wherein the stabilizer is a divalent cation, an oxygen radical scavenger, an antioxidant, an ethylene inhibitor, a compound that intercalates into the lipid bilayer of the cell or a heat-shock protein.

19. The method of claim 18 wherein the ethylene inhibitor is an ethylene biosynthesis inhibitor or an ethylene action inhibitor.

20. The method of claim 1 further comprising the step of storing the cryopreserved cell at said cryopreservation temperature for a period of time of greater than one month.

21. The method of claim 20 wherein the period of time is greater than one year.

22. A method for recovering cryopreserved plant cells comprising the steps of:

a) cryopreserving plant cells according to the method of claim 1;

b) thawing the cryopreserved plant cells to a temperature above freezing;

c) incubating the thawed plant cells in a growth medium containing a stabilizer;

d) removing the cryoprotecting agent; and e) recovering viable plant cells.

23. The method of claim 22 wherein the stabilizer is a divalent cation, an oxygen radical scavenger, an antioxidant, an ethylene inhibitor, a compound that intercalates into the lipid bilayer of the cell or a combination thereof.

24. The method of claim 23 wherein the growth medium further contains a cyroprotectant.

25. The method of claim 1 wherein the cryoprotection solution contains a divalent cation, which may be the same or different from the divalent cation used in preculturing.

26. The method of claim 1 wherein preculturing is performed simultaneously with loading and the osmotic agent and the cryoprotecting agent are the same.

27. The method of claim 1 wherein preculturing is performed simultaneously with vitrifying and the cryoprotection solution contains the osmotic agent.

28. A method for cryopreserving a plant cell comprising the steps of:

preculturing the plant cell with a divalent cation at greater than about 5 mM and an osmotic agent for a period of time effective to stabilize cell membranes;

loading the plant cell with a cryoprotecting agent;

vitrifying the plant cell with a cryoprotection solution; and freezing the vitrified plant cell at a cryopreservation temperature.

* * * * *